(12) United States Patent
Tamari

(10) Patent No.: US 7,591,812 B1
(45) Date of Patent: Sep. 22, 2009

(54) PASSIVE VENOUS AIR PURGING CHAMBER WITH VENT/SUCKER BLOOD HANDLING CAPABILITIES

(76) Inventor: Yehuda Tamari, 21 Singworth St., Oyster Bay, NY (US) 11771

( * ) Notice: Subject to any disclaimer, the term of this patent is extended or adjusted under 35 U.S.C. 154(b) by 323 days.

(21) Appl. No.: 11/491,853

(22) Filed: Jul. 24, 2006

Related U.S. Application Data

(63) Continuation-in-part of application No. PCT/US2005/002198, filed on Jan. 24, 2005.

(60) Provisional application No. 60/538,277, filed on Jan. 22, 2004.

(51) Int. Cl.
*A61B 19/00* (2006.01)
*A61M 37/00* (2006.01)
*A61M 1/14* (2006.01)

(52) U.S. Cl. .......................... 604/406; 604/6.15; 422/44

(58) Field of Classification Search ................ 604/4.01, 604/5.01, 6.01, 6.07, 6.09, 6.1, 6.11, 6.15, 604/319, 320, 405, 410, 403, 408; 422/44
See application file for complete search history.

(56) References Cited

U.S. PATENT DOCUMENTS

| | | | |
|---|---|---|---|
| 4,424,190 A | 1/1984 | Mather, III | |
| 4,959,062 A | 9/1990 | Gellman | |
| 5,049,146 A | 9/1991 | Bringham | |
| 5,382,227 A | 1/1995 | Riquier | |
| 5,484,474 A | 1/1996 | Weinstein | |
| 5,512,042 A | 4/1996 | Montoya | |
| 5,573,526 A * | 11/1996 | Hess | ........................... 604/408 |
| 5,720,741 A | 2/1998 | Stewart | |
| 5,823,986 A | 10/1998 | Peterson | |
| 5,876,611 A | 3/1999 | Shettigar | |
| 5,935,093 A | 8/1999 | Elgas | |
| 6,019,824 A | 2/2000 | Schnell | |
| 6,050,968 A | 4/2000 | Van Driel | |
| 6,287,270 B1 | 9/2001 | Fini | |
| 6,302,860 B1 | 10/2001 | Gremel | |
| 6,337,049 B1 | 1/2002 | Tamari | |
| 6,524,267 B1 | 2/2003 | Gremel | |
| 6,537,495 B1 | 3/2003 | Cambron | |
| 6,773,426 B2 * | 8/2004 | Tamari | ....................... 604/406 |
| 6,773,670 B2 | 8/2004 | Stringer | |

(Continued)

OTHER PUBLICATIONS

Tamari, Y: A New Top-Loading Venous Bag Provides Vacuum Assisted Venous Drainage. Perfusion 17:383-390, 2002.

(Continued)

*Primary Examiner*—Leslie R Deak

(57) ABSTRACT

The invention is a closed complaint venous reservoir with at least one pliable wall having at least three innovative features: 1) the venous reservoir incorporates means that purge gas bubbles entering the venous reservoir without the user intervention, 2) the venous reservoir incorporates a cardiotomy reservoir, and 3) the pliable wall of the venous reservoir is sealed within a rigid housing allowing control of its "atmospheric" pressure, and therefore the pressure at which that wall collapses. The combination of the three innovative features provides a collapsible compliant reservoir unitized with cardiotomy reservoir having air removal features and enabling vacuum augmented venous drainage (VAVD) that match that of the open hardshell venous-cardiotomy reservoir unit, while retaining the advantages of the closed soft shell venous reservoir.

61 Claims, 8 Drawing Sheets

U.S. PATENT DOCUMENTS

| | | |
|---|---|---|
| 6,852,280 B2 | 2/2005 | Vijay |
| 6,908,446 B2 | 6/2005 | Yokoyama |
| 7,131,966 B1 * | 11/2006 | Tamari ................. 604/406 |
| 2001/0010802 A1 * | 8/2001 | Tamari ................. 422/41 |
| 2004/0197223 A1 | 10/2004 | Olsen |
| 2004/0220509 A1 | 11/2004 | Olsen |

OTHER PUBLICATIONS

Medtronic's Resting Heart Module Instructions for Use.
Terumo's Reduced Prime Optimized Circuit (ROC Safe).
Cobe's (Sorin's) ECC.o and Synergy.
Terumo's bubble trap.
Cardiovention's Instructions for Use for the CORx System.

* cited by examiner

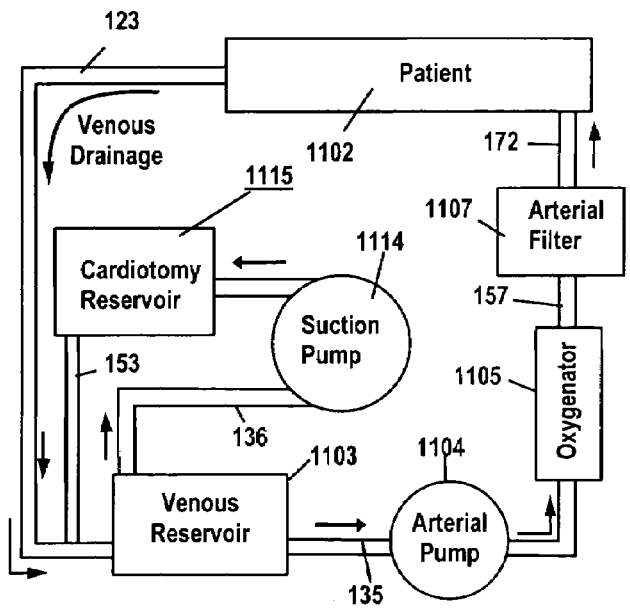
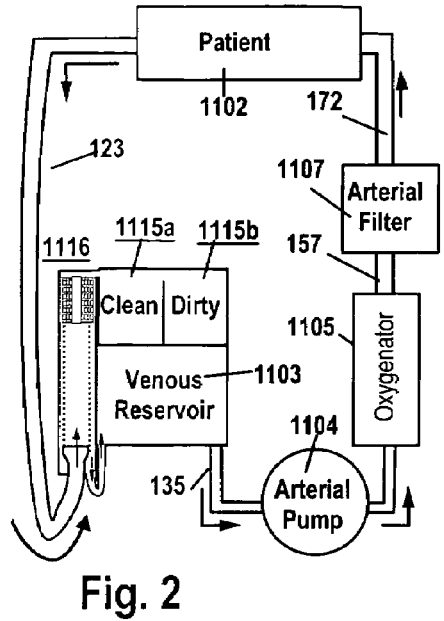
Fig. 1 PRIOR ART
Fig. 2
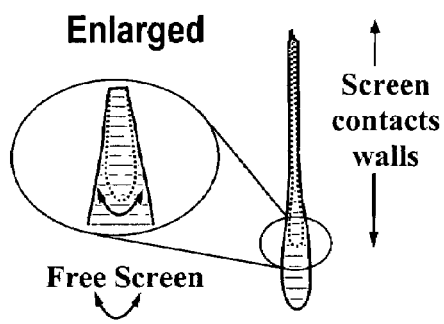
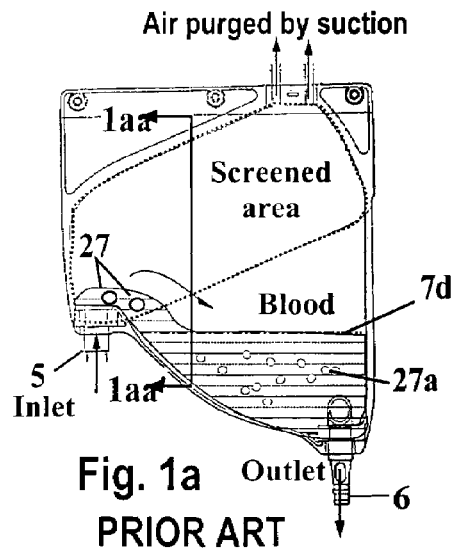
Fig. 1ab Fig. 1aa
PRIOR ART
Fig. 1a Outlet
PRIOR ART

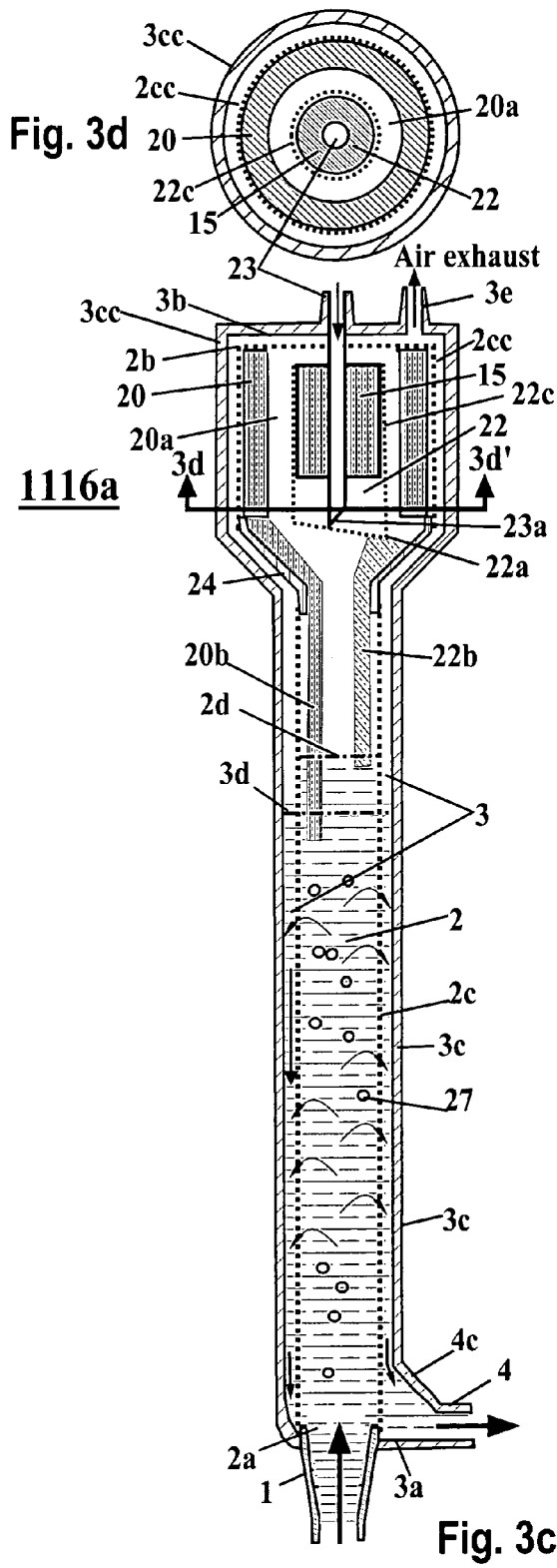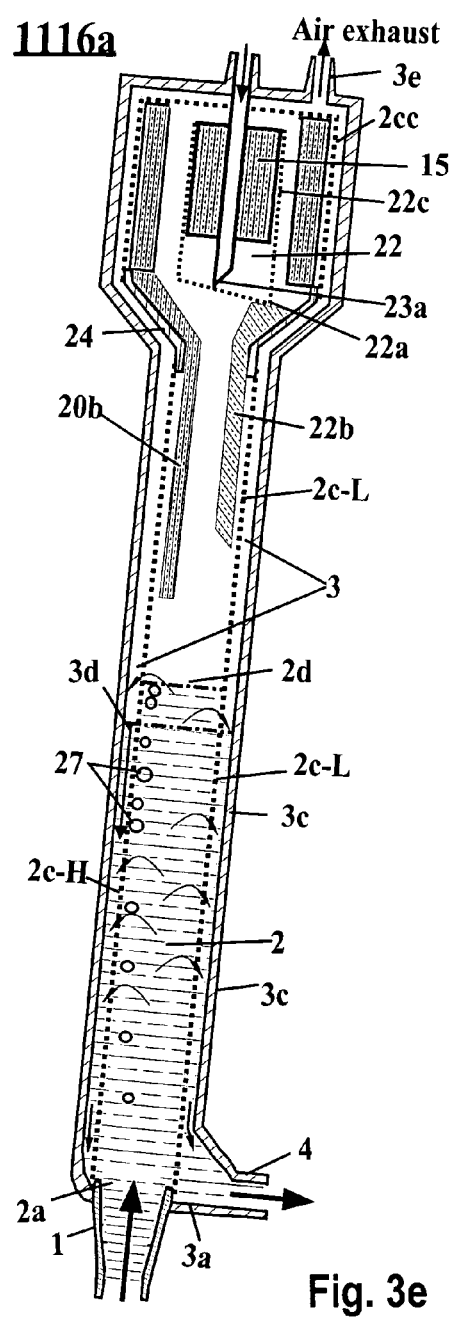

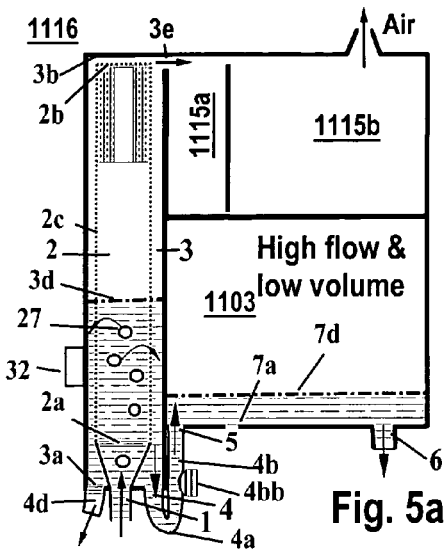
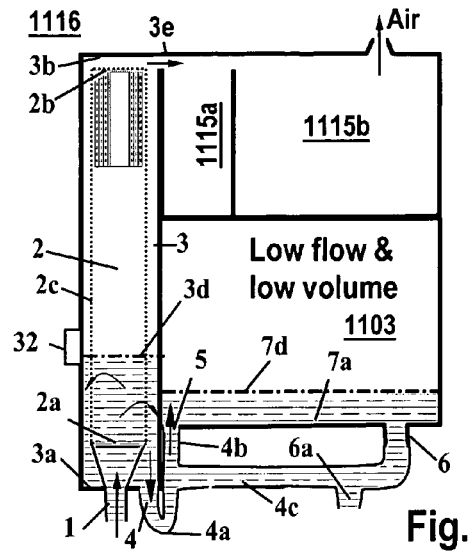
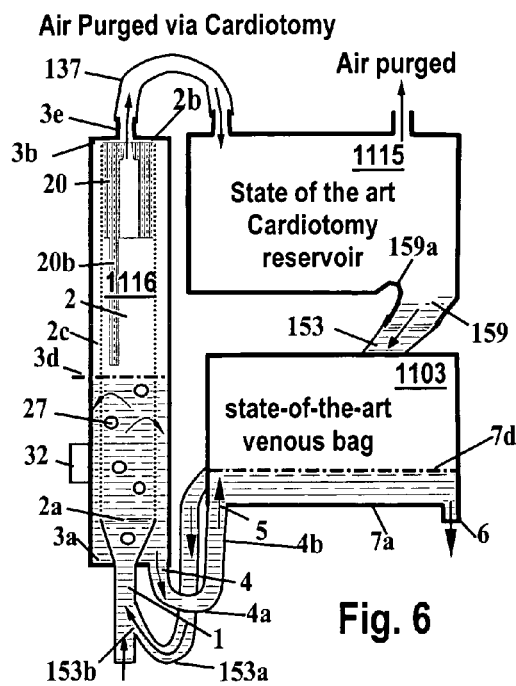
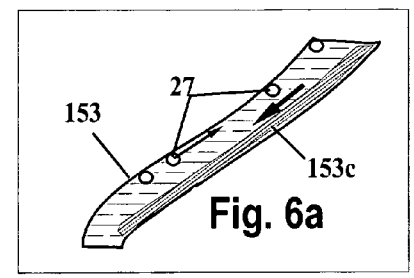
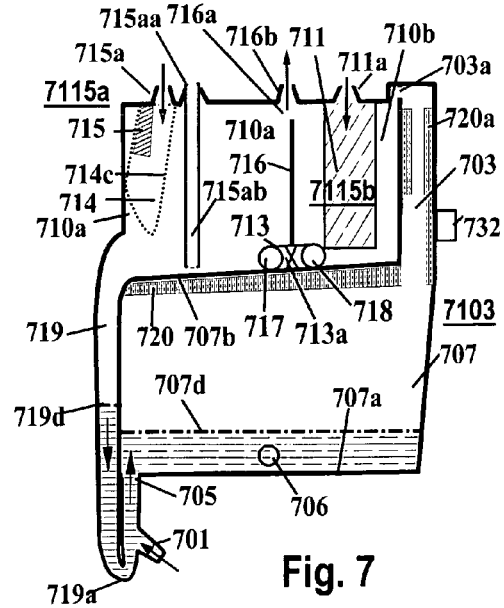

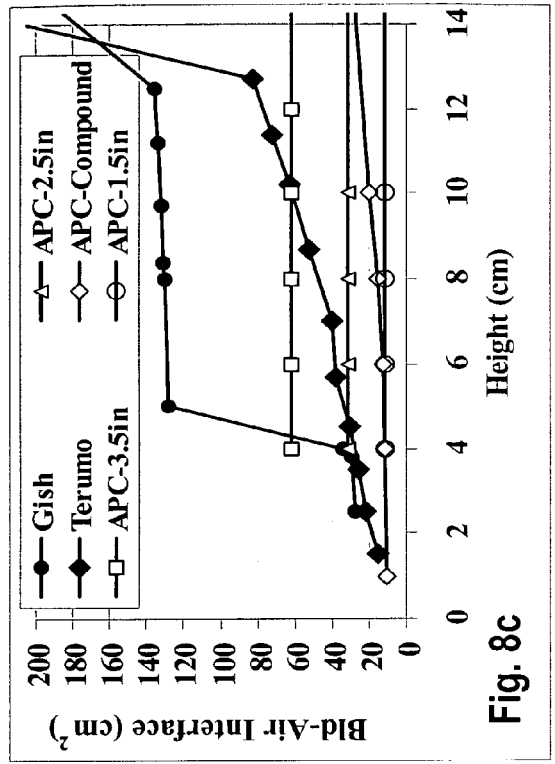
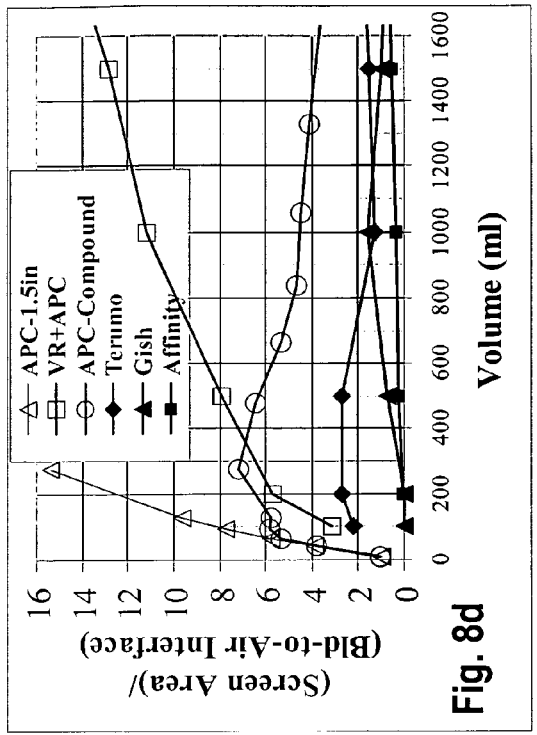
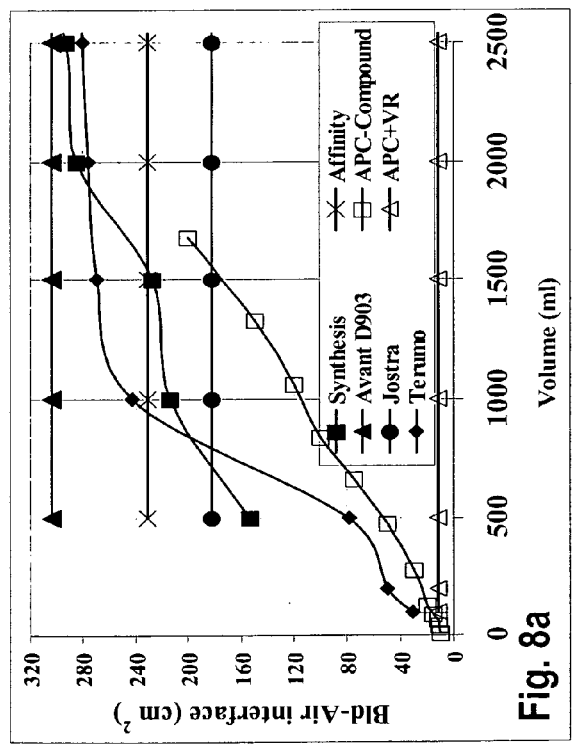
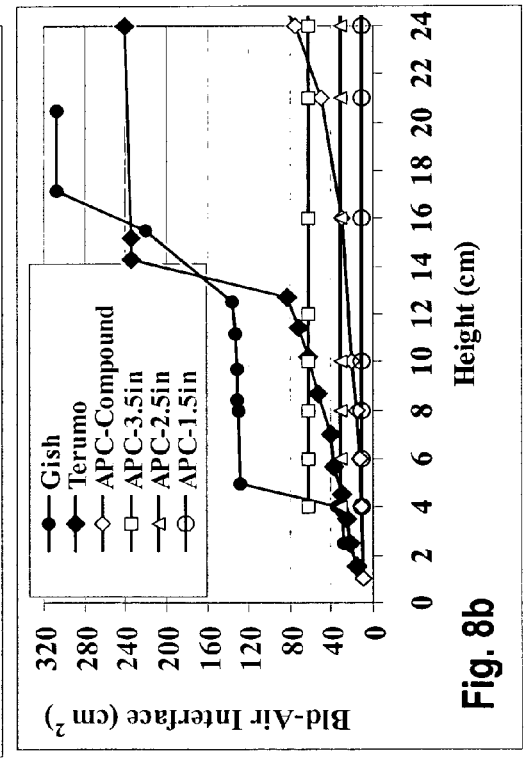
Fig. 8a
Fig. 8b
Fig. 8c
Fig. 8d

PASSIVE VENOUS AIR PURGING CHAMBER WITH VENT/SUCKER BLOOD HANDLING CAPABILITIES

CROSS REFERENCE TO RELATED APPLICATIONS

This application is a Continuation-in-Part of International Application number PCT/US2005/002198 filed Jan. 24, 2005 titled "A Soft-Shell Venous reservoir-Cardiotomy Reservoir with Improved Air Removal Capability" and published under the PCT as WO 2006/057650 A2 Jun. 1, 2006 that claims the priority date of the provisional Patent Application Ser. No. 60/538,277 filed Jan. 22, 2004, the disclosures of those applications being incorporated herein by reference thereto.

GOVERNMENT INTERESTS

This invention was in part made with government support under SBIR Grants # R44HL-55034 and R44-HL66810 awarded by the National Institute Health, National Heart, Lung, and Blood Institute. As such the government may have certain rights in the invention.

BACKGROUND OF THE INVENTION

1. Field of the Invention

The full invention consists of an air purging system in combination with a compliant storage chamber having at least one pliable wall that forms a venous reservoir and a two-chamber cardiotomy reservoir incorporated atop the storage chamber. The combined units provide a collapsible "closed" venous reservoir unitized with cardiotomy reservoir, with vented blood separated from the sucker blood, having air removal features that improve that of a hardshell venous-cardiotomy reservoir unit. The innovative characteristics of each of the three devices support their use on their own.

2. Description of the Prior Art

During cardiopulmonary bypass, blood flow from the venous side of the patient to a venous reservoir depends on the resistance of the fluid conduit between patient and reservoir and the pressure difference between patient and reservoir. When the reservoir is maintained at atmospheric pressure, that pressure difference is the height difference between patient and reservoir; the resulting flow is referred to as gravity drainage. Venous drainage by gravity alone provides inadequate return during procedures such as minimally invasive cardiac surgery and bypass via femoral cannulation. Usually it is the resistance of the venous cannula that limits the flow rate. Vacuum assisted venous drainage (VAVD) is a technique that overcomes flow limitations by applying suction to the venous reservoir thereby increasing the pressure difference between the venous cannulation site and venous reservoir. VAVD allows for a decrease in the inner diameter (ID) of the venous line, thereby reducing prime volume and enabling the use of a smaller internal diameter cannula, which translates to an easier insertion, better surgical view and a smaller surgical incision.

Clinically, venous bags are used because they provide significant safety features: if the bag accidentally empties, it collapses, thereby preventing gross air from being pumped to the patient, they have no, or very little, air-blood interface, and they require no antifoam agents that can embolize into the blood. Designs that allow VAVD with venous bags have been previously described by Tamari's U.S. Pat. Nos. 6,337,049 and 6,773,426, and Cambron's U.S. Pat. No. 6,537,495. The present invention also allows the user the option of VAVD.

The only venous reservoir that combines a flexible wall and a rigid wall to form a "closed" variable blood chamber is that described in U.S. Pat. Nos. 4,424,190 and 4,959,062. Each of these devices has its outlet at the lowest point of the venous reservoir (see 24 in FIG. 24 of U.S. Pat. No. '062, and 36 in FIG. 3 of U.S. Pat. No. '190). This choice makes it more difficult to assure that the pliable wall seals against its mating rigid wall when the reservoir empties. The '190 patent has a drawback: once that reservoir empties, its pliable wall is sucked in at its outlet and shuts off as it should. However, when the volume returns, the flexible wall remains stuck to the outlet and does not open until the reservoir is almost full. The '062 patent's design alleviates that flaw however it introduced another problem: when the reservoir empties the rib prevents the flexible wall from completely sealing against the outlet port allowing air from the cardiotomy reservoir to be sucked in, an undesirable outcome. The present invention provides a design that allows the outlet to close completely when the reservoir empties and to easily open when less than ⅓ of the volume of a full reservoir returns.

When air enters blood, the blood foams. Hard shell reservoirs have defoamers within the venous inlet chamber (e.g. see defoamer 6 in distribution chamber 22 of FIG. 1 in Fini, U.S. Pat. No. 6,287,270). In the open, hard shell reservoir, air escapes by floating to the top of the reservoir where it is purged to atmosphere. In prior art venous bag reservoirs, air also floats to the top but it must be actively eliminated. This can be done manually with a syringe, or more frequently with a roller pump intermittently operating to remove air accumulating at the top of the bag. This is shown in FIG. 1 where foam that accumulates at the top of collapsible venous reservoir 1103 is removed by suction pump 1114 that pumps that foam/air to cardiotomy reservoir 1115. With either method, a sudden large volume of air can overwhelm the air removal system and cause disastrous consequences, especially without a vigilant perfusionist. Further, sucking blood and foam through the small diameter of the tubes and stopcocks used at the top of current bags results in blood damage. Various solutions have been proposed. Tamari's U.S. Pat. Nos. '049 and '426 eliminate air from a venous bag automatically by utilizing a floating ball valve, a hydrophobic membrane, or a level sensor. All three systems require suction to remove the air. Also, with current available membrane materials, the membrane has limited effective life.

Tamari's '049 and '426 patents also describe a blood chamber with a level sensor that activates a vacuum source to remove the air when the blood level in the chamber drops below that sensor. The design provides automated means to remove air from that chamber and that chamber in combination with a blood chamber having at least one flexible wall allows automated air removal and VAVD with a venous bag but does not, as the present invention, allow for passive air removal.

Active air removal required for venous bags also results in more difficult priming. Thus, once a bag is primed and the prime solution is recirculated, the air in the rest of the circuit is returned to the bag, again filling it with air. A better system would not allow air to return to the primed bag. This would reduce priming time and the possibility that air can remain in the bag.

State-of-the-Art soft-shell venous reservoirs with a screen are poorly designed: a large portion of their screen contacts the internal walls of the bag rendering that portion of the screen ineffective and thereby increasing the resistance to blood flow across the screen. This is illustrated in FIG. 1a, a line drawing of a prior art bag made by Cobe, FIG. 1aa, a line drawing of a cross section along line 1aa-1aa' of the bag shown in FIG. 1a, and FIG. 1ab, an enlargement of the circled section of the bag shown in FIG. 1aa. As illustrated, at low volume most of the screen contacts the walls of the bag and is unavailable for blood flow. The contact area of the screen contacting the walls of the bag increases as the volume in the reservoir decreases. Two typical prior art venous bags exhibiting these problems are the ones described in Hess's U.S. Pat. No. 5,573,526 and in Stewart's U.S. Pat. No. 5,720,741. The latter is depicted in the present application in FIG. 1a as PRIOR ART. One aspect of the present invention eliminates contact between the screen and the walls of the chamber housing it, thereby allowing the use of a screen with smaller area and/or smaller pores. Though Tamari's '049 and '426 patents illustrate designs that prevent the screen from contacting the wall of the reservoir, (e.g. FIGS. 7a and 7b of '049), those designs in combination with a venous reservoir require that controlled vacuum be applied to the top of the venous bag to remove air.

As the pore size of filter screen used to trap bubbles decreases so does the effective open area and resistance to flow. For example, the preferred screen used for State-of-the-Art venous bag has a pore size of 105μ and an open area of 52% as compared to an open area of only 30% for a screen with a pore size of 37μ. However, as described in reference to screen 2c in FIG. 3a, the use of smaller pore screen reduces the size and number of bubbles. The larger effective screen area of the present invention allows using a smaller pore size screen and still maintaining a total open area that is equal to, or is even larger than, State-of-the-Art bags thereby maintaining a blood velocity across the screen that equals to or is lower than that associated with current bags. A lower velocity translates to lower number of bubbles crossing the screen.

At low blood levels, or if there is air in current soft shell reservoirs, the indication of blood level is inaccurate and the alarms, mostly designed for hard shell reservoirs, are not reliable. The present invention provides more reliable means to alarm at low blood levels.

A softshell reservoir with integrated cardiotomy reservoir is described in Elgas's U.S. Pat. No. 5,935,093. That softshell blood reservoir incorporates an integral flexible cardiotomy section in which a filter/defoamer unit is supported in a semi-rigid cage. The reservoir also incorporates a storage section and a mixing section. The three sections can selectively communicate with each other. A major shortcoming of this unit is that if the cardiotomy, in fluid communication with the venous reservoir, empties, then air can enter the venous reservoir and exit its outlet. The unit also does not allow VAVD and requires active removal of air from the venous reservoir. The present invention prevents air from the cardiotomy to exit the venous reservoir, allows VAVD and air is exhausted to atmosphere passively.

Almost all hard shell venous reservoirs incorporate a cardiotomy reservoir; the user gets a single unit (e.g. Thor et al's U.S. Pat. No. 5,411,705 and Fini's '270 patent). The lower cost, shorter setup time and ease of air removal are the major reasons that more hard shell reservoirs are used than collapsible venous reservoirs. In one form, the present invention provides the user with a collapsible venous reservoir and a cardiotomy reservoir as a single unit that is easy to setup, and is clinically safer than the State-of-the-Art unified hard shell venous-cardiotomy reservoir unit.

During CPB, "clean" blood includes blood aspirated from a venting site (e.g. the aortic root cardioplegia cannula, LV vent), blood with entrapped air withdrawn from the top of a venous bag (i.e. as used by NovoSci), and blood purged from the top of the arterial filter. Clean blood is distinctly different from the "dirty" blood sucked from the surgical field, mostly of which comes from the pericardial sack. Before clean blood is returned to the patient, its entrapped air must be removed. Vent blood may entrain a large volume of air. If that blood is added directly to venous blood, it generates a large volume of foam (and a concomitant large blood-gas area) and can easily overwhelm the active air removal systems of current minicircuits (see below). Before sucker blood can be returned it must be filtered to remove both debris (e.g. particles of fat and tissue, clots) and entrapped air. Retransfusion of cardiotomy suction blood and mediastinal shed blood increases postoperative systemic inflammatory response, hemolysis, acellular lipid deposits in the microvasculature, thrombin, neutrophil, and platelet activation, and the release of neuron-specific enolase. It is considered preferable to send this blood to a cell saver. When using venous bags both the clean and dirty blood are processed by passing through a cardiotomy reservoir, a disadvantage because the clean blood is exposed to the inlet of the filter for the dirty blood with its aforementioned deleterious consequences.

There are no cardiotomies that filter the clean blood separate from the dirty blood and keep the two apart. Some State-of-the-Art hard shell reservoirs allow clean blood to bypass the dirty blood filter by directing the clean blood into the venous blood inlet chamber. However, none provide means to purge the air out of the clean blood prior to it combining with the venous blood, thereby limiting the clinically undesirable generation of large volume of blood foam. Fini's '270 patent partially addresses this by having a valve that lets the user to either use the dirty blood (flow to the venous chamber) or to accumulate it in a chamber and then direct it to a cell saver. Yokoyama, et al.'s U.S. Pat. No. 6,908,446 illustrates a cardiotomy reservoir with a filter for the vented blood and a separate filter for dirty blood. This prevents clean blood from directly contacting foreign substances filtered off from the dirty blood but does not prevent clean blood accumulating in the cardiotomy from contacting the debris in the filter once the blood level reached the debris. The present invention addresses these drawbacks by separating the clean blood from the dirty blood as well as giving the user a choice to return the dirty blood to the bag or to a cell saver.

Blood enters the cardiotomy reservoir of prior art devices either at the top of the cardiotomy or via a tube that extends vertically downward to the bottom half of the reservoir. The former separates blood from air as it enters the reservoir but results in foam from the entering blood splashing into the blood in the reservoir. The latter, when the blood level is above the outlet of the entrance tube, results in foam from the air in the entering blood bubbling in the blood in the reservoir. The present invention allows at least the clean blood to enter along an angle that purges most of the air prior to the clean blood joining blood already in the cardiotomy while limiting splashing.

Many of the State-of-the-Art cardiotomies include a perfusion connector that accommodates a ⅜" ID tubing, but none have a ⅜" ID tubing extending from the top of the cardiotomy to its bottom as to allow a clotted cardiotomy filter to be bypassed using a new cardiotomy connected to the inlet of that ⅜" tubing.

Cardiotomy reservoirs are also used to accommodate the overflow of blood volume that exceeds the capacity of the venous bag (the largest one can accommodate less than 2.0 L). Larger blood volume capacity is frequently required during aortic or mitral valve replacement during which the excess volume rises into the cardiotomy reservoir resulting in clean venous blood contacting the aggressive filter and the filtrate (e.g. fat, bone chips etc.) trapped at the bottom of the filter of the cardiotomy reservoir that can result in the aforementioned undesirable outcomes.

The blood level at which the clean blood contacts the antifoam loaded defoamer in the venous reservoir and the volume at which the blood contacts the aggressive cardiotomy reservoir filter is summarized in Table 1 for typical State-of-the-Art hard shell venous-cardiotomy reservoir units. In one form of the present invention, the volume capacity of the closed venous blood chamber and/or the "clean" chamber of the cardiotomy reservoir is higher than current systems, thereby limiting clean blood contact with the "dirty" chamber and/or defoamer while limiting blood-to-air interface (see below).

Minimizing the blood-to-air interface is a major design objective of devices used in the cardiopulmonary bypass circuit. The last two columns in Table 1 provide the surface area of air that the blood is exposed to when the reservoir contains 500 or 1000 ml of blood. As will be shown, when the venous reservoir of the present invention is filled, it has 7 to 30 times smaller blood-to-air area than State-of-the-Art hard shell venous reservoirs. The values assume that there is no air in the venous blood or foam above the blood. It should be noted that the maximum venous blood volume that can be accommodated by the State-of-the-Art units without contacting the defoamer, of either the HSVR or CR, or the dirty blood filter is 1,200 ml.

TABLE 1

Nominal values for adult Prior Art hard shell reservoirs v. the present invention.

| Model | Volume to contact HSVR* Defoamer | Volume to contact CR** | Blood-Air area at | |
|---|---|---|---|---|
| | | | 500 ml | 1000 ml |
| One form of the present Invention*** | 3,000 ml | 3500 ml | <20 cm² | <20 cm² |
| Terumo - Capiox 18SX | 3,000 ml | 1,200 ml | 78 cm² | 240 cm² |
| Dideco - Synthesis | 600 ml | 1,400 ml | 155 cm² | 213 cm² |
| Dideco - Avant 903 | 600 ml | 3,500 ml | 303 cm² | 303 cm² |
| Jostra - VHK 4200 | 300 ml | 500 ml | 181 cm² | 181 cm² |
| Medtronic - Affinity CVR NT | 1,000 ml | 400 ml | 232 cm² | 232 cm² |
| Cobe - VVR4000i | 200 ml | 800 ml | | |
| Gish - CAPVRF 44 | 1200 ml | 1200 ml | 131 cm² | 135 cm² |

*HSVR—Hard shell venous reservoir,
**CR—Cardiotomy reservoir,
***Typical values

The defoamer of State-of-the-Art venous reservoirs is located at least along the top section of the reservoir (e.g. Terumo's SX-25) or lineup the entire screen area of the inlet section of the reservoir (Cobe's VVR 4000i). Currently it is not known whether early collapsing of blood foam that lowers blood-air interface but increases blood contact with the antifoam, is clinically better than reducing blood contact with the antifoam but increasing blood-to-air interface. One aspect of the present invention incorporates a top and bottom defoamer, wherein the bottom defoamer is smaller by volume and extends downward from the top defoamer into the inlet chamber of the air purging chamber, a geometry that provides flexibility in adjusting early defoaming capabilities while reducing the defoamer contact with the blood.

Blood flow from the cardiotomy reservoir to a venous bag can be intermittent or continuous depending on the frequency the suckers are used and the volume aspirated from the field.

The outlet port of the cardiotomy reservoir used for adults is universally ⅜" internal diameter as is the tube connecting the outlet of the cardiotomy reservoir to the inlet of the venous bag (see tube 153 in FIG. 1). Further, the outlet port faces straight vertically or horizontally. That combination results in the air in tube 153 to be trapped by the incoming blood above it, and dragged with that blood into the venous bag thereby adding air to the blood in the venous bag. A form of the present invention provides a fluid path between the cardiotomy reservoir and venous bag with decreased tendency to trap air.

Unpublished studies by the Inventor have shown the efficiency to remove venous air while minimizing blood volume and blood damage by blood contacting air can be expressed by a dimensionless parameter that equals the ratio of screen area available for blood flow between the venous inlet and outlet and the blood-to-air interface area. A higher ratio should result in better clinical outcome. The values for that parameter for some State-of-the-Art hard shell venous reservoirs are given in FIGS. 8c and 8d at a range of volumes. The data suggests that Terumo's hard shell venous reservoir (e.g. Capiox 18SX) should handle venous air best. Unpublished studies by the Inventor confirmed that Terumo's 18SX has the lowest bubble count at its outlet when air is added to the venous blood flowing into its inlet. FIGS. 8c and 8d also show that the values of the dimensionless parameter for the present invention (i.e. APC and VR+APC) are significantly higher than Terumo's values. For that reason, as well as others described below, the present invention handles air better than any other State-of-the-Art venous reservoir.

Hard shell venous reservoirs utilize low level detectors to either shut the arterial pump and/or actuate a tubing clamp (e.g. see Sorin's ECC.O system below) to stop outlet flow from the reservoir and prevent the reservoir from emptying and air from being pumped to the patient. A higher change in blood level per change in volume (i.e. a reservoir with smaller cross sectional area) allows for a control more sensitive to smaller changes in blood volume in the reservoir. As shown in FIGS. 8a and 8b, Terumo's hard shell venous reservoirs have the smallest cross sectional area with the highest blood level of any State-of-the-Art reservoirs. At low volumes, Terumo's reservoirs also have the largest screen area and smallest blood-to-air interface, see FIG. 8d. The present invention improves on these parameters, providing an elongated, small diameter air purging chamber with a larger screen area and smaller blood-to-gas interface per blood volume.

Numerous minicircuits that minimize operating volume and eliminate the blood-to-air interface have been introduced (e.g. Cardiovention's CORx covered by U.S. Pat. No. 6,773,670, Medtronic's Resting Heart system covered by U.S. Pat. Nos. 6,302,860, 6,524,267, Terumo's Reduced Prime Optimized Circuit also called $ROC_{SAFE}$ and Sorin's ExtraCorporeal Circulation Optimized, ECC.O). Each of these circuits has replaced a venous reservoir with a venous air filter to trap and remove air from the venous line and the cardiotomy reservoir. The premise of these circuits is to reduce prime volume to reduce hemodilution. Lower priming volume results in a reduction in post-bypass transfusions, reduces crystalloid fluid administration and retains plasma colloid osmotic pressure during CPB, and reduces post-CPB extravascular lung water and weight gain (edema).

Terumo's minicircuit includes an air sensor that controls both the centrifugal pump and an electronic venous occluder that allow the user to remove the air manually. Stopping blood flow to remove air may be clinically harmful, especially in cases where air enters the venous line repeatedly.

Medtronic's, CardioVention's and Cobe's minicircuits utilize a sensor that detects air in the venous line and actuates suction to remove that air and the associated electronics assure that the suction is applied only when so indicated by the sensor. Doing otherwise removes blood from the reservoir or risking air entering the outlet of the air purging chamber. A more recent invention is described by Olsen et al in US Patent Application number 20040220509 entitled "Active air removal from an extracorporeal blood circuit". That design requires complicated electronics as displayed by FIGS. 14 through 56 of that application.

The greatest weakness of the State-of-the-Art minicircuits is their poor air removal characteristics and lack of compliance between the patient and the centrifugal (arterial) pump. Each of the active air removal systems requires a special controlling system that senses air and applies suction to remove all the air from the top of the venous filter. This requires the user to assist the upward rise and removal of air by reducing blood flows by as much as 50%. Thus, in cases where air is intermittently entrained in the venous line, the user has to reduce the blood flow to the patient repeatedly. Cobe recommends that the roller pump removing air from the venous line be set to pump 450 ml/min for 6 sec each time air is sensed in the venous line. In a worst-case scenario, 0.5 cc of air in the venous blood passing the air sensor every 6 sec (5 cc/min of air) would result in pumping over 400 ml of blood every minute out of the CPB circuit and into the cell saver or cardiotomy. Even if the air removal pump is actuated once per minute due to a small air bubble in the venous line, a patient on bypass for 90 minutes would lose 45 ml/min or, in aggregate, over 4 L. Medtronic's Active Air Removal Device and Venous Air Removal Device (VARD) can be fooled by foam that forms at the top of the venous filter, a shortfall that can result in removal of a significant volume of blood. This is especially true at high blood flow rates and may be the reason that the Medtronic's' instructions warn that blood flow should be reduced to 1.0 L/min for 30 sec at least once every hour. Further, per the "Instructions for Use", wall suction is used to remove the air and therefore, the blood sucked with the air is also lost. Later instructions suggested that the cell saver's cardiotomy be used instead of wall suction. However, large blood volumes directed to the cardiotomy exposes that blood to the aforementioned harmful affects of the filtrate of the dirty blood, the antifoam agents, and to the large blood-air interface associated with the defoamer of the cardiotomy, all of which degrade the benefits of the minicircuits. A form of the present invention provides efficient venous air removal unmatched by any minicircuit, or State-of-the-Art hard shell or soft shell reservoirs.

The air purging chambers of State-of-the-Art minicircuits essentially placed arterial filters in the venous line. These filters' ratio of height to diameter is less than 2 and they do not communicate with ambient atmosphere. This design is not conducive to detecting small changes in volume. The present invention provides a much larger height to diameter ratio and a much larger change in height for the same change in volume, a characteristic that allows level sensors to react to much smaller volume changes.

A major objective for "venous filters" with air removal capabilities is to reduce the priming volume of the CPB circuit by removing the venous reservoir while still removing air and foam from the venous line prior to it entering the arterial pump. At least one aspect of the present invention provides further reduced volume and effectively, passively or actively, deaerates venous blood and collapses foamed blood, much like hard-shell venous reservoirs do. This action is achieved without the need to reduce pump flow or suck blood out of the circuit, and requires less contact with the defoamer while lowering foam volume (by defoaming the blood earlier), without exposing venous blood to the "dirty" blood of a cardiotomy, and with minimal or no blood loss due to air removal.

None of the minicircuits enables the user to handle clean blood except through the cell saver, which mandates a loss of plasma and platelets. The present invention deaerates clean blood before it is combined with venous blood without requiring it to pass through either a cardiotomy reservoir or a cell saver. In one form this is achieved with a two chamber cardiotomy, one chamber for the dirty blood and the other for the clean blood, with means that allow the user to start or stop blood flow from the dirty to the clean blood. Blood from the clean blood chamber is in fluid communication with the inlet of the venous reservoir.

All minicircuits utilize a centrifugal pump (CP) to draw venous blood (Kinetic Assisted Venous Drainage or KAVD) and generate arterial line pressure. KAVD has 2 major draw backs:

1. Centrifugal pumps handle air poorly; any large bubbles that pass the air-removal system and enter the centrifugal pumps are divided into much smaller bubbles that are less buoyant and are thus more difficult to remove. Large bubbles that could be trapped at the top of the arterial filter appear as smaller bubbles, able to cross the arterial filter. This problem is further exacerbated at the higher pump speeds needed when a single centrifugal pump is used both to draw venous blood and to generate the arterial line pressure.

2. Centrifugal pumps maintain a fixed pressure difference between inlet and outlet. Thus, when the heart is manipulated causing the venous cannula to temporarily obstruct, venous flow stops. Flow cessation due to occlusion upstream of the pump inlet results in an inlet suction at least equivalent to the positive pressure at the centrifugal pump's outlet before the flow stopped. For example, at a flow of 5 L/min and a pump outlet pressure of +250 mmHg, an obstruction at the pump inlet would translate to the pump generating an inlet pressure of −250 mmHg or higher. A high transient suction applied at the tip of the venous cannula could suck the vessel against the cannula's open end, causing it to occlude, preventing further flow, and perhaps causing both intima and blood damage until the pump is stopped. This condition may also result in cavitation (bubble formation within the pump), a situation that could result in significant blood damage. The present invention operates in the safer VAVD mode that allows the user to set a maximum negative pressure with a vacuum regulator yet allow reverting to operating in the KAVD mode. In either the KAVD or VAVD mode of operation, the system provides better air handling than current venous reservoirs or removes air from the venous blood before it reaches the bubble dispersing centrifugal pump. Further, the presence of air at the top of the air purger of the present invention provides compliance that reduces the spikes of negative pressure inherent with current KAVD minicircuits by allowing the pump controller more time to decrease pump flow and absorbing the large pressure spikes associated with sudden stoppage of blood flow at the pump inlet. Unlike all other minicircuits, the present invention, besides providing a choice between KAVD and VAVD, also allows venous drainage by gravity. Further in gravity mode it may incorporate passive means that prevent blood from spilling over the top of the blood chamber.

When vacuum is applied to State-of-the-Art blood reservoirs then the water vapor at 37° C. of the air being purged condenses on the cooler walls of the vacuum tubing and can drip back into the blood thereby compromising sterility. Current systems eliminate that problem by inserting a sterile vapor trap between the vacuum source and the blood chamber. This increases setup time and cost. The present invention incorporates a vapor trap thereby eliminating the need for a stand alone trap.

Current vacuum assisted venous drainage capable bags (e.g. See FIG. 4 of the Instruction for Use for The V-Bag) require one connection to apply vacuum to the rigid chamber housing the bag and another to apply vacuum to the cardiotomy. A single connection to both venous bag and cardiotomy chambers would reduce setup and cost.

The aforementioned shortfalls of the State-of-Art minicircuits, venous reservoirs (whether bags or hard shell) and cardiotomy reservoirs are improved upon by the innovative designs of the present invention as more fully described below.

BRIEF SUMMARY OF THE INVENTION

The present invention in its simplest form consists of a very efficient, low volume, chamber that removes air from the venous line, hereinafter referred to as the air purging chamber (APC). The air purging chamber consists of a vertical blood chamber having an inlet, an outlet and an air purge port. The inlet and outlet preferably separated by a screen that allows blood to cross from the inlet to the outlet but retains air bubbles in the inlet chamber. The screen also defines an inlet chamber and an outlet chamber. Gas (e.g. air) bubbles in the blood entering the bottom of the inlet chamber rise to the top of the blood column contained by the inlet chamber and are purged to atmosphere. The air purging chamber separates air bubbles from the venous blood and purges that air to atmosphere as is the case with the hard shell venous reservoir without the need for the suction or vacuum required with prior State-of-Art soft-shell venous reservoir or minicircuits. A defoamer, located at the top of the inlet chamber, collapses foam that forms by the air bubbles in the blood. The blood in the inlet chamber flows across the screen into the outlet chamber and downward towards the outlet port located along the bottom of the outlet chamber. Combining this air purger with a cardiotomy reservoir and a reservoir having at least one flexible wall as a single unit provides venous reservoir with superior air removal characteristics, with the safety benefits of prior art collapsible venous reservoirs while avoiding such disadvantages as air entrapment, required vigilance for air removal, poor level control, slower priming, and lack of a cardiotomy reservoir. The functionality of this innovative venous reservoir is further enhanced by also providing VAVD capabilities with a built-in vapor trap, a small blood-to-gas interface even when the venous reservoir is full. The innovative cardiotomy with a separate chamber for clean blood and separate chamber for dirty blood and a vapor trap completes this superior design.

From the brief description of the invention and the aforementioned drawbacks of current reservoirs and venous air purging of minicircuits, it is the objective of the present invention to provide an improved venous air purging chamber that provides bubbles entering its inlet a path to move unhindered upward and passively purged to atmosphere and that can operate either with VAVD where suction is utilized to remove air or by gravity drainage, where the venous air is removed passively to atmosphere.

In one preferred embodiment, the top of the air purging chamber is designed to also accept deaerated vented blood without it contacting the dirty blood in the cardiotomy reservoir.

In another preferred embodiment, the top of the air purging chamber also incorporates means to deaerate and defoam vented blood without it mixing with the dirty blood in the cardiotomy reservoir.

It is another form the present invention provides an improved venous air purging chamber with defoaming capabilities.

Yet another objective of the present invention is to provide an improved low volume venous air purging chamber with a large effective screen area available for blood flow that provides defoaming capabilities and that, in one form, accepts clean blood without that blood being exposed to dirty blood.

Yet another objective of the present invention is to provide an improved venous air purging chamber with a large effective screen area available for blood flow having a lower operating volume than State-of-the-Art air purgers used for minicircuits.

Yet another objective of the present invention is to provide an improved passive venous air purging chamber having a large effective screen area and a low operating volume that for the adult patient its blood-to-air interface area is lower than 30 $cm^2$ for at least 8 cm of its lower height and or 60 $cm^2$ for at least 13 cm of its lower height.

Another objective is to provide a venous air purger acting as a venous reservoir that provides a "tall" and relatively narrow liquid column having a ratio of height to diameter greater than 2 such that even at low blood volumes a large screen area is still available for blood flow and, relative to State-of-the-Art reservoirs, large changes in height correspond to small changes in volume.

It is another objective of the present invention to provide an improved venous air purging chamber that provides defoaming capabilities even at low filling volume while minimizing blood contact with the defoamer.

It is another objective of the present invention to provide a blood chamber with defoaming capabilities that incorporates a top and bottom defoamer, wherein the bottom defoamer has a lower volume, is longer and extends downward into the blood chamber. Such chamber can for example be the venous air purging chamber.

Another objective is to provide a cardiotomy reservoir having at least a clean blood and a dirty blood chambers as a single unit with the clean and dirty chambers in a fluid communication that can be closed or opened by the end user.

Another objective is to provide fluid communication between the outlet of an air purging chamber and the inlet to a compliant storage chamber that is, at least in part, formed of the rigid structure.

Another objective is to provide a compliant blood chamber that once primed remains air free.

Another objective is to provide a compliant storage chamber with at least one pliable wall that once primed, it shuts off prior to air entering it.

Another objective is to provide a fluid path between an air purging chamber and a compliant storage chamber with an adjustable resistance to liquid flow thereby allowing the user to adjust the height of the blood column in the air purging chamber and thereby increase the screen area available for blood flow.

Yet another objective of the present invention is an improved venous blood reservoir, having at least one pliable wall combined with a cardiotomy reservoir in fluid communication such that a single air port can be used to apply the same vacuum to the blood in each of the chambers.

One more objective of the present invention is to incorporate a vapor trap in the vacuum side of the air purging chamber, the cardiotomy reservoir or compliant blood chamber, said trap replacing a stand alone vapor trap thereby reducing cost and setup time.

Another objective of the present invention is to provide an improved venous blood reservoir with at least one pliable wall having passive means to eliminate air.

Yet another objective of the present invention is to provide a venous reservoir with at least one flexible wall combined with a cardiotomy as a single unit that can be used with either gravity drainage or with VAVD thus, reducing cost of inventory and simplifying the user's set up.

A further objective of the present invention is to provide a single unit composed of a venous blood reservoir having at least one pliable wall in fluid communication with at least a second blood chamber said second chamber having at least one rigid wall wherein the blood level in the second chamber can be higher than the blood level of the chamber with the pliable wall.

A further objective of the present invention is to provide a venous blood reservoir having at least one pliable wall and at least second blood chamber having at least one rigid wall wherein the second chamber is located above the venous reservoir and the chambers combined as a single unit with an outlet that, once primed, shuts off before air can exit its outlet.

A further objective of the present invention is to provide a venous blood reservoir and a cardiotomy reservoir combined as a single unit with the venous blood reservoir able to handle a blood flow of 6 l/min and accommodates at least 1,300 ml without the venous blood contacting a defoamer and/or the filter of the dirty blood.

A further objective of the present invention is to provide a venous blood reservoir having at least one pliable wall and a cardiotomy reservoir combined as a single unit and with the cardiotomy consisting of a clean blood chamber and a dirty blood chamber, said cardiotomy chambers in fluid communication with each other via a fluid path that can be opened/closed by the user.

A further objective of the present invention is to provide a cardiotomy reservoir consisting of a clean blood chamber and a dirty blood chamber; said chambers in fluid communication with each other, and means that allow the user to open/close said fluid communication.

A further objective of the present invention is to provide a blood path between the outlet of a cardiotomy reservoir and a second chamber that incorporates means that limit the volume of air entrapped and pumped from the cardiotomy reservoir into the second chamber.

A further objective of the present invention is to provide a venous blood reservoir with improved passive air removal capabilities, having a blood volume capacity of at least 300 ml and a flow capacity of at least 5 l/min, wherein the venous blood-to-air interface is no more than 50 $cm^2$ for at least the lower 10 cm of the blood reservoir.

A further objective of the present invention is to provide a stand-alone venous air purging chamber with passive and improved passive air removal capabilities even when operating at a blood volume less than 150 ml that can handle a blood flow of at least 4 l/min.

Yet another objective is to offer the combination of a rigid air purging chamber and a venous reservoir having at least one flexible wall with passive air removal capabilities.

One more objective of the present invention is to provide a venous air purging chamber with passive and improved air removal capabilities having a ratio of screen area to blood-to-air-interface area of at least 4.0.

Another objective of the present invention is to provide the manufacturing flexibility to accommodate future clinical finding that could determine which is more beneficial to the patient: collapsing the foam to reduce blood-gas interface or reducing blood contact with the defoamer.

Other objectives, features and advantages of the present invention will become apparent by reference to the following detailed description, an illustrative description not to be taken as limiting the present invention, of the presently preferred embodiments thereof with reference to the accompanying drawings therein.

BRIEF DESCRIPTION OF THE DRAWINGS

FIG. 1 is a line drawing of the pertinent components of a typical cardiopulmonary bypass circuit showing the prior art soft shell venous reservoir and a single chamber cardiotomy reservoir.

FIG. 1a is a line drawing illustrating that at a low blood level in a prior art venous bag the effective screen area is very small relative to total area of the screen in the bag and that suction is required to remove air entering the bag.

FIG. 1aa is a line drawing of a cross section along line 1aa and 1aa' of prior art bag shown in FIG. 1a illustrating that at low blood volume very little of the screen of this bag is available for blood flow.

FIG. 1ab is a line drawing of an enlargement of the circled section of the bag shown in FIG. 1aa showing that at low volume with the prior art bag very little of the screen is available for blood flow.

FIG. 2 is a line drawing of the pertinent components of a typical cardiopulmonary bypass circuit showing the soft shell venous reservoir integrated with the air purging chamber and a two chambered cardiotomy reservoir of the present invention.

FIG. 3aa is a line drawing illustrating a means to prevent blood from overfilling the air purging chamber using a vertically extended air exhaust tube.

FIG. 3b is a line drawing illustrating another view of the air purging chamber illustrated in FIG. 3a taken along line 3b-3b' of FIG. 3a.

FIG. 3c is a line drawing of the front view of another preferred embodiment of the present invention illustrating a venous air purging chamber similar to that illustrated in FIG. 3a that also incorporates a deaerating and defoaming chamber for vented (clean) blood.

FIG. 3d is a line drawing illustrating another view of the air purging chamber illustrated in FIG. 3c taken along line 3d-3d' of FIG. 3c.

FIG. 4b is a line drawing illustrating another cross sectional view of the air purging chamber combined with the venous and the two chambers cardiotomy reservoir illustrated in FIG. 4a taken along line 4b-4b' of FIG. 4a.

FIG. 4c is a line drawing illustrating another cross sectional view of the air purging chamber combined with the venous and cardiotomy reservoir illustrated in FIG. 4a taken along line 4c-4c' of FIG. 4a.

FIG. 4d is a line drawing illustrating another cross sectional view of the air purging chamber combined with the venous and cardiotomy reservoir illustrated in FIG. 4a taken along line 4d-4d' of FIG. 4a.

FIG. 5a is a line drawing illustrating the blood level in the air purging chamber relative to the blood level in the venous reservoir at high flow and low volume conditions.

FIG. 5b is a line drawing illustrating the blood level in the air purging chamber relative to the blood level in the venous reservoir at low flow and low volume conditions.

FIG. 6 is a line drawing illustrating the air purging chamber used with State-of-the-Art venous bag and an innovative cardiotomy reservoir that limits air from being dragged along its exit tubing into the air purging chamber.

FIG. 6a is a line drawing illustrating the exit tubing into the air purging chamber shown in FIG. 6 and the direction of flow of blood and air bubbles.

FIG. 7 is a line drawing illustrating a cardiotomy and a compliant chamber combined as a single unit by sharing a common rigid wall.

FIG. 8a presents data comparing the blood-to-air interface area of the present invention (VR-APC) to that of the State-of-the-Art venous reservoirs as a function of blood volume.

FIG. 8b presents data comparing the blood-to-air interface area of the present invention (VR-APC) to that of the State-of-the-Art venous reservoirs as a function of the height of the blood in the reservoir.

FIG. 8c presents the data of FIG. 8b expanding the lower volume range.

FIG. 8d presents the ratio of the screen area available for venous blood flow to the area of the blood-to-air interface of the present invention (APC and VR+APC) to the State-of-the-Art hard shell venous reservoir.

DETAILED DESCRIPTION OF THE INVENTION

Figure 3A:
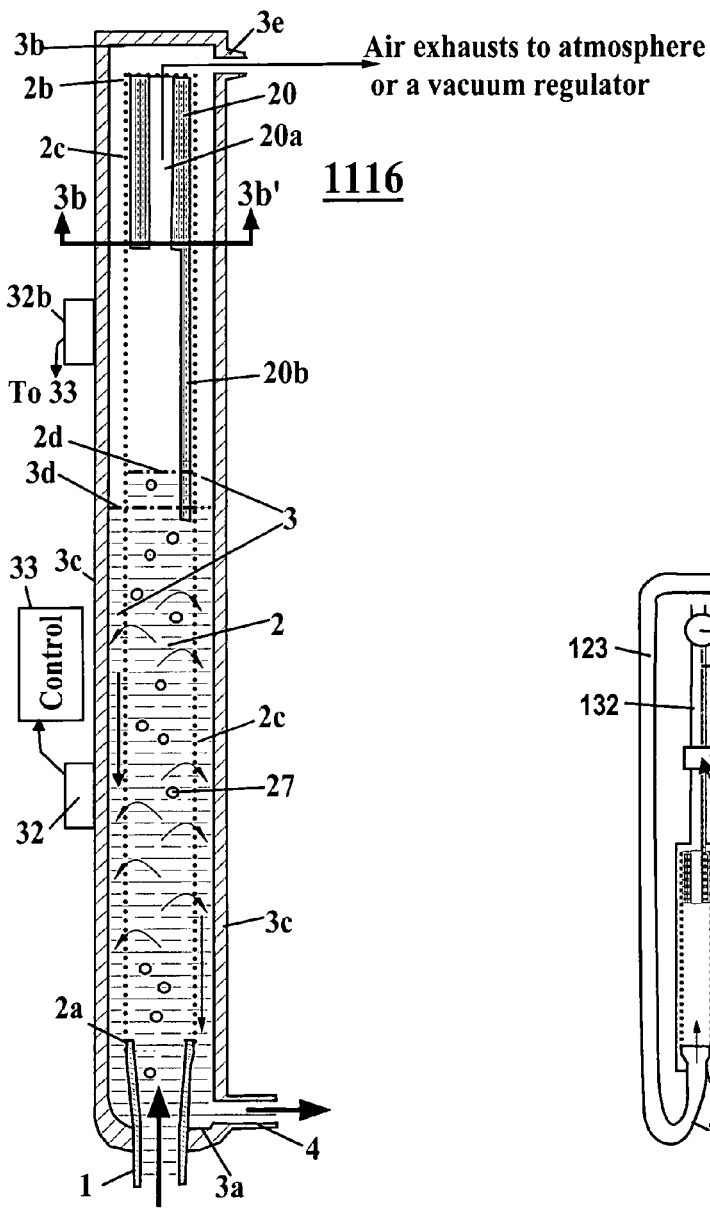
FIG. 3a is a line drawing of the front view of one preferred embodiment of the present invention illustrating a venous air purging chamber that purges air without the user input.

Reference should now be made to the drawings wherein the same reference numerals are used throughout to designate the same or similar parts. It should be noted that the use of cardiopulmonary bypass, as shown in FIG. 1, is for descriptive purposes, and should not be taken as a limitation to the use of the devices described hereinafter. Further, the description of the inventions that follow are for illustrative purposes, other embodiments are possible, and therefore what follows is suggestive of the art but should not be construed as a limitation of the scope or the spirit of the invention. Hereinafter, unless otherwise indicated, the terms soft-shell venous reservoir, venous bag and bag are used interchangeably and refer to a blood chamber with at least one flexible wall.

FIG. 1 is a schematic representation of a typical cardiopulmonary bypass circuit according to the prior art showing the location of the venous reservoir relative to the patient and the other components in the circuit. Tubing 123, receiving venous blood from patient 1102, is coupled to venous reservoir 1103. The blood is drawn from venous reservoir 1103 via tube 135 by arterial pump 1104 and pumped through membrane oxygenator 1105 wherein oxygen is supplied to the blood and carbon dioxide is removed. The blood from the oxygenator flows via tubing 157 to arterial filter 1107 and then via tubing 172 and an arterial cannula (not shown) back to the patient. One main function of the venous reservoir is to eliminate air contained in the venous blood before it is pumped back to the patient. Air that enters venous bag 1103 rises to the top of the reservoir. This air can not be passively removed to atmosphere, but requires active removal as shown in FIG. 1 where the air is pumped out by suction pump 1114 into cardiotomy reservoir 1115. Suction pump 1114 is usually one of 3 to 5 pumps composing a heart-lung machine, which is part of a hardware required for cardiopulmonary bypass. The defoamed blood is returned from cardiotomy reservoir 1115 back to venous bag 1103 via connecting tubing 153. As described in the Description of the Prior Art, blood flowing in tubing 153 can entrain air that is then pumped into the venous bag, a non-desirable outcome.

The ineffective air handling of prior art soft shell venous reservoirs is illustrated by line drawings given in FIGS. 1a, 1aa and 1ab. FIG. 1a is a line drawing of State-of-the-Art venous reservoir as typically represented by Cobe's venous reservoir (Model # VRB, Cobe Lakewood, Colo. and described in U.S. Pat. No. 5,352,218, issued to Buckley, et al. Oct. 4, 1994 titled "Venous reservoir bag assembly"). Though this bag has a large screen (defined by the dashed lines in FIG. 1a), at low volumes only a very small area of the screen (defined by the double headed arrow in FIG. 1ab) is available for blood entering the screen area to flow to the outlet port. This is further exasperated at low blood volume, the bag is not fully expanded at the screen area causing most of the screen, defined by the double arrow, to contact the collapsed walls and not available for blood flow. At low volumes and high flow, large bubbles 27 entering the Cobe bag are dragged across the screen and break up into smaller bubbles (27a) that are more difficult to remove due to their lower buoyancy. As described below in reference to FIGS. 5a and 5b, the present invention provides a larger screen area for blood flow at a lower blood volume.

FIG. 1a also illustrates that air removal from State-of-the-Art venous reservoirs having at least one pliable wall requires active suction. Thus air is removed with a syringe or usually with one of the roller pumps (e.g. 1114) sucking the air out.

FIG. 2 is a schematic representation of a system according to present invention showing the relative location of the collapsible venous reservoir in a typical cardiopulmonary bypass circuit and the incorporation of the air purging system. The circuit shown in FIG. 2 is identical to FIG. 1, except that in FIG. 2, venous bag 1103 of the present invention incorporates cardiotomy reservoir with chamber 1115a for "clean" blood and separate chamber 1115b for "dirty" blood as well as incorporating air purging chamber 1116. Incorporating the cardiotomy reservoir eliminates the need for tubing 136 between the top of the collapsible venous reservoir and cardiotomy reservoir 1115 and suction pump 1114 required for the prior art systems shown in FIG. 1. If desired, the fluid communication between cardiotomy 1115a and air purging chamber 1116 can be made, as well known in the art, via perfusion connecting ports and perfusion tubing.

Figure 3B:
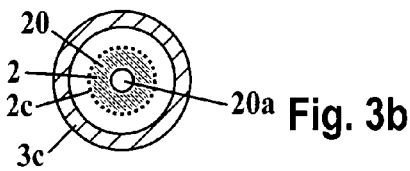
Figure 3A:
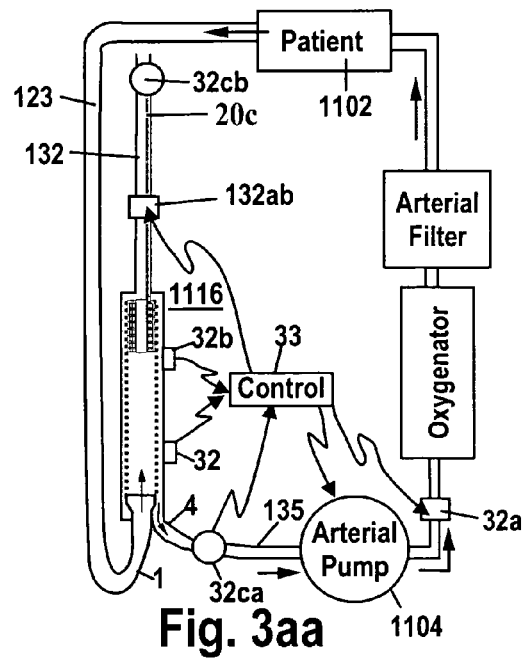

FIGS. 3a and 3b are line drawings of a front view and top view, respectively, illustrating one preferred embodiment of air purging chamber 1116. In general, the air purging chamber is a disposable consisting of an inlet chamber and an outlet chamber having a common screened wall. Screen wall 2c forms at least a portion of the outside wall of inlet chamber 2 and at least a portion of the inside wall of outlet chamber 3. While there are various configurations that can be used to form the air purging chamber, one of the more efficient and simpler designs is illustrated by FIGS. 3a and 3b, and 3c and 3d. Blood enters inlet chamber 2 via inlet port 1. Inlet chamber 2 is a vertical cylinder defined by screened wall 2c that extends from its bottom level 2a to its top level 2b. The internal diameter of chamber 2 preferably is larger than the internal diameter of inlet port 1. As shown, inlet port 1 extends, and expands in diameter into outlet chamber 3 formed by rigid walls 3c and is sealed to bottom 2a of inlet chamber 2 to form a continuous fluid path with inlet chamber 2. The screened walled cylinder forming inlet chamber 2 is housed in, and preferably is centrally located along its axis within a second cylindrical structure formed by rigid vertical wall 3c forming outlet chamber 3. Venous blood that contains air bubbles 27 enters air purging chamber 1116 via inlet port 1 into inlet chamber 2. Bubble movement upward in chamber 2 is enhanced by the larger diameter of inlet chamber 2 relative to that of the inlet port. The large internal diameter reduces the blood velocity thereby reducing drag and allowing longer time for the bubbles to move upward. Lower velocity also lowers the tendency of larger bubbles to break into smaller ones; larger bubbles have higher buoyancy and less of a chance of crossing screen 2c into outlet chamber 3. With sufficient pressure across screen 2c, bubbles can cross into chamber 3 and travel to outlet 4 of chamber 3, a very undesirable outcome. The upward direction of blood flow at inlet 1 further enhances desirable upward movement of the bubbles. It should be noted that by extending the top most level 2b of screen 2c to level 3b of outlet chamber 3 limits the chance of air crossing into outlet chamber 3. Though not shown, it should be obvious that inlet port 1 can be positioned along top 3b with a tubing connected to its bottom and extending downward into inlet chamber 2, much like many of the State-of-the-Art hard shell venous reservoirs.

The effective area of screened wall 2c is defined as the area available for blood in inlet chamber 2 to flow across screen 2c into outlet chamber 3. For air purging chamber 1116 that area equals the product of the periphery of screen wall 2c (i.e. 3.14×diameter of chamber 2) and the height difference between blood level 3d in chamber 3 and bottom level 2a of chamber 2. Because none of the screen area in contact with the blood (wetted area) is blocked by the walls 3c of outlet chamber 3, as is the case with State-of-the-Art venous bags discussed in reference to FIGS. 1a, 1aa and 1ab, blood flows across that entire wetted area. A larger effective area translates to lower velocity across each pore in the screen which lowers the drag force that can push bubbles across that screen into outlet chamber 3. Once the blood enters outlet chamber 3, it flows downward in the annular space defined by cylindrical screen wall 2c and rigid wall 3c until it exits through outlet port 4. Outlet port 4 in fluid communication with outlet chamber 3 is located at a vertical level that is preferably lower than bottom level 2a of screen 2c, a location that reduces the chance of bubbles crossing from inlet chamber 2 to the outlet port 4. However, if minimizing operating volume is more important then the outlet can be located at level 2a. Air entering inlet chamber 2 may cross to outlet chamber 3 along a non wetted screen area and then flow upward to air exhaust tube 3e, or escape along the top of chamber 2.

Air purging chamber 1116 preferably incorporates defoamer 20 (preferably made of reticulated polyurethane foam having a pore size in the range of 5 to 50 ppi treated with antifoam agents such as silicone) that breaks up foam formed by air traveling up the blood column in inlet chamber 2. Defoamer 20 preferably is located at the top most section of inlet chamber 2, a location that limits its contact with the blood in chamber 2 but avails it to defoam blood foam that rises to the top of chamber 2. The defoamer may also incorporate open channel 20a that provides unrestricted fluid communication between inlet chamber 2, the top of chamber 3, and air exhaust port 3e utilizing structure 20c. Air is exhausted via channel 3e in wall 3c to atmosphere. Thus, foam (very large bubbles) entering channel 20a is exposed to defoamer 20 where it is broken up and collapsed. For cases where excess foam is generated, or if defoamer 20 loses some of its defoaming capacity, then having outlet of channel 3e directed from exhausting to atmosphere to the inlet of a cardiotomy reservoir, as shown in reference to tube 137 in FIG. 6, and defoamer 15cc illustrated in FIGS. 4a and 4b where further defoaming can be achieved.

Since foam has a very a large blood-to-air interface, it is advantageous to limit its life and collapse it sooner rather than later. To that end, an additional length of a defoamer, 20b, is used. Defoamer 20b preferably has a nominal width equaling to 10% to 50% of the inside periphery of inlet chamber 2, and extends from the bottom of defoamer 20, downward up to 75% of the length of inlet chamber 2. It may also have a smaller surface area than defoamer 20. These dimensions reduce the undesirable blood contact with the defoamer yet still collapse blood foam that has not reached defoamer 20 and thereby significantly reducing the blood to gas interface associated with foam. The variable defoaming capabilities achieved by varying the width to less than the perimeter of chamber 2 and extending the defoamer into the blood chamber accommodates future clinical finding that would optimize which is more beneficial to the patient: collapsing the foam to reduce blood-gas interface or reducing blood contact with the defoamer.

The dimensions of air purging chamber 1116 are balanced between decreasing the velocity of the blood and increasing the screen area to enhance bubble removal (i.e. large internal diameter) and limiting the prime volume (i.e. smaller internal diameter). It should also have low resistance to blood flow. With that in mind, it has been determined that for an air purging chamber designed for adult patients, the optimum internal effective diameter of outlet chamber 3 is between 7/8" and 2.0" (having a horizontal cross sectional area of 4 to 32 $cm^2$) and inlet chamber 2 preferably has a nominal internal diameter that is 1/8" to 3/16" smaller than that of the outlet chamber. Another definition of the effective diameter of the inlet chamber is such that it results in annular cross sectional area (area of the outlet chamber less that of the inlet chamber) of at least 1 $cm^2$, or the effective cross sectional area between that of a 3/8" ID tubing (0.71 $cm^2$) and that of 1/2" ID tubing (1.27 $cm^2$). The preferred cross sectional area of the annular space between the inlet and outlet chamber can also be defined as approximating the cross sectional area of venous line 123 shown in FIG. 2. The effective diameter is the average diameter of the chamber, (e.g. for an ellipse it would be average of the major and minor diameters). The height of inlet chamber 2, when used in combination with a venous bag, is preferably greater than the maximum blood level in the venous bags, or typically between 7" and 22".

When air purger 1116 is used for minicircuits without a venous reservoir, then its height can be as low as 4", a height that can be extended with a smaller diameter tube as described hereinafter in reference to tube 132 shown in FIG. 3aa. The screen filter is preferably made of medical grade polyester, or from other appropriate blood compatible material, having a pore size between 20μ and 150μ but most preferably having a pore size between 20μ and 40μ. Most preferably the outlet chamber has an internal diameter between 1.25" and 1.75" and a height that prevents blood level 2d in inlet chamber 2 from contacting defoamer 20 even when the bag is filled. Blood still may contact extended defoamer 20b. The top of the screen preferably extends to the top of the outlet chamber and may be closed at its top, a design that limits the blood foam crossing the defoamer radially and spilling into the outlet chamber.

When air purger 1116 is used as a stand alone device or in combination with a cardiotomy as for example shown by FIG. 5a less venous bag 1103, then it is advantageous to provide it with a larger volume capacity. This can be achieved using the design dictated by the aforementioned dimensionless of the ratio of screen area available for blood flow between the venous inlet and outlet and the blood-to-air interface area. As shown in FIG. 8d, the largest ratio for State-of-the-Art hard shell venous reservoirs is below 3. Since a larger dimensionless ratio (larger screen area for blood flow and/or lower blood gas interface area) is clinically advantageous, the air purger incorporates dimensions, for the adult patient, that provide a ratio that is at least 4 when operating at 100 ml without a complaint venous reservoir and at 300 ml when operating with a complaint venous reservoir. This design allows for a combination of diameters composed of long small diameter at the bottom and a shorter larger diameter at the top. In some respect this design simulates current hard shell venous reservoirs but its much larger ratio renders it superior.

A larger volume for the stand alone unit can also be achieved by either having a larger diameter top, as for example shown in FIG. 3c, or increasing the effective diameter of outlet chamber 3 as its height increases. Typical values for such a unit are illustrated in FIGS. 8b and 8c by the data labeled "APC-Compound". Note that the cross sectional area of these higher volume capacity units still have a blood-to-air interface that is significantly lower than State-of-the-Art venous reservoirs. Unlike present reservoirs, the venous air purger always provides a blood-to-air interface area that is less than 40 cm² for at least the first 10 cm from bottom 3a of outlet chamber 3 and less than 60 cm² for at least the first 14 cm from bottom 3. Should a higher blood level in chamber 3 lower gravity drainage, then vacuum applied to air exhaust port 3e compensates for that shortfall.

Defoamer 20 preferably has an OD equal to the internal diameter of chamber 2 and a length of ¾" to 6". If the defoamer is to be supported by the screen, then the OD of defoamer 20 can be slightly larger than the internal diameter of inlet chamber 2, thus the slightly compressed defoamer inserted into chamber 2 would spring back and its outer surface grab the inner surface of chamber 2. The inside diameter of open channel 20a is preferably between ⅛" and ½", a diameter that allows free air flow yet maximizes the volume of defoamer per unit length.

It should be pointed out that the most preferred dimensions, at a prime volume of 100 ml, provide a nominal screen area of 110 cm², a total screen area that is smaller than the most other venous bags (e.g. the screen used in Cobe's bag is 200 cm²). Further, as the pore size of filter screen used to retain bubbles decreases, the effective open area decreases and the resistance to flow increases. The preferred screen used for State-of-the-Art venous bags has a pore size of 105μ with an open area of 52%. However, the use of smaller pore screen reduces the size and number of bubbles that cross screen 2c. A test comparing bubble counts at the outlet of the air purging chamber showed that when 130 cc/min of air are pumped into a 6 L/min blood flow entering the venous air purging chamber, the bubble counts of 15μ size bubbles were 6,410, and 763 bubbles/min for screens having a pore size of 37μ, 65μ and 85μ respectively. The smaller pore size screen had significantly lower bubbles crossing despite its lower open area (31% for the 37μ, 38% for the 65μ and 46% for the 85μ pore size screens). For a preferred internal diameter of 1.2" for chamber 2, a screen with a pore size of 37μ having an open area of 31%, the open area per one inch height of screen is over 1.1 in². Since the screen makes no contact with wall 3c of outlet chamber 3, its entire wetted area is available for blood flow. It is the larger effective screen area of the present invention that allows using a smaller pore size screen and still maintaining a total open area that is equal to, or is even larger than, State-of-the-Art venous bags thereby maintaining a blood velocity across the screen that equals to or is lower than that associated with current venous bags. Lower velocity translates to lower number of bubbles crossing the screen.

As with many devices handling blood outlet chamber 3 preferably is made of clear biocompatible thermoform plastic such as PETG, PVC or polycarbonate or other similar materials. The entire blood contacting surfaces of air purging chamber 1116, and if possible the defoamer too, are preferably passivated by one of the many coats available such as the heparin coating by Carmeda (Carmeda AB, Upplands Vasby Sweden.)

The preferred dimensions and the design of venous air purging chamber provide a smaller diameter air remover than State-of-the-Art venous or arterial filters and allow the user to operate at a lower blood volume in line with minicircuit technology while providing superior air handling that includes passive air elimination. This is illustrated by FIGS. 8a, 8b, 8c and 8d.

It should be understood that the aforementioned specifications are for illustrative purposes and that other combination of dimensions can also achieve desirable results. For example, the circular cross sections can be replaced with elliptical, star, or rectangular cross sections. The design of the air purging chamber is not limited to the designs shown in FIGS. 3a and 3b. For example the air purging chamber can also be effective by incorporating some of the designs suggested for arterial filters (e.g. U.S. Pat. No. 5,484,474 or 4,743,371) or bubble traps (e.g. U.S. Pat. No. 6,019,824).

It should be further understood that the aforementioned specifications are given for adult patients with expected blood flow between 4 and 7 L/min. The specifications can be easily scaled down to accommodate lower flows and lower prime volumes associated with pediatric and infant patients. Scaling can utilize well know equation relating resistance to flow as a function of cross sectional areas, such as Poiseuille law dictating flow, Q, to be a function of diameter, d, to the fourth power, $Q=f(d^4)$ while still having the diameter of the inlet chamber sufficiently large to allow bubbles to float freely up the blood column. For example, for infants on bypass using ¼" internal diameter tubing as venous line 123 in FIG. 1, the nominal internal diameter of inlet chamber of the air purging chamber can be ⅜" and the internal diameter of the outlet chamber can be 1/16" to 3/32" larger.

The air purging chamber can incorporate means assuring that, when inflow exceeds outflow, blood does not overfill reaching and spilling out of exhaust port 3e. One such means is level sensor 32b shown in FIG. 3a. Thus, when sensor 32b detects that the blood level in outlet chamber 3 is too high, it sends a signal to alarm the user and/or to controller 33 that increases pump speed to accommodate the increased inflow from the patient and prevent blood overflowing chamber 3. The controller can also actuate tubing clamp 132a placed on air exhaust tube 132 shown in FIG. 3aa to close tube 132 thereby preventing blood from rising to further and spilling. The placement of sensor 32b can be adjustable to preferably prevent venous blood from contacting main defoamer 20, but if clinically necessary, moved higher to allow blood level 2d to reach defoamer 20 but still prevent blood from spilling out.

Another and a simpler means that assures blood does not overfill and spills from the air purging chamber is shown in FIG. 3aa. Here, air exhaust tube 132 extends vertically up so its open end is leveled approximately at the level of the patient's heart. Thus, when venous inflow exceeds flow out of the air purging chamber, then the blood level in the tube 132 rises, reducing gravity drainage (the height difference between the patient and blood level in the air purger) and decreasing venous flow from the patient. Venous inflow stops once the blood level in tube 132 reaches the level of the patient. The internal diameter of tube 132 is preferably at least ⅜" but more preferably is at least ½".

The air purging chamber can also incorporate blood level maintaining means for maintaining the blood level in chamber 3 above outlet port 4 thereby preventing gross air (as opposed to microbubbles) from exiting the outlet blood chamber. As an example, sensor 32 on wall 3c operably connected to controller 33 is attached to wall 3c of outlet chamber 3 in FIGS. 3a, and 3aa and is used as a low level sensor that maintains blood level 3d at a safe level above outlet 4 of chamber 3. When detector 32 senses that the blood level dropped below a safe level, it sends a signal to control unit 33. Control unit 33 is capable of at least sounding an alarm, slowing down or shutting off the arterial pump, clamping off outflow (e.g. via tube clamp 32a), or increasing inlet flow (e.g. during VAVD, increasing the vacuum—not shown) to assure that blood level 3d does not reach outlet port 4 causing air to exit outlet port 4. Level detectors already incorporated in State-of-the-Art heart-lung machines can be used for this purpose. Thus the combination of State-of-the-Art control units and the innovative disposable air purging chamber, provides the user a system that effectively purges air out of the venous line passively and automatically while preventing air from exiting outlet 4 of air purging chamber 1116. It should be pointed out that the rigid wall of air purging chamber 1116 can be easily adapted to the State-of-the-Art level detectors. This is in contrast to the difficulties encountered when trying to use these level detectors by placing the sensor on the pliable wall of current venous bags. As described above, the air purging chamber acts much like a hard shell reservoir except that its blood-to-air interface area and hold up volume are significantly lower.

The combination of adjustable means to limit the high and low levels of blood in air purger 1116 also allows adjustment of the maximum operating blood volume in outlet chamber 3 and inlet chamber 2. For example, a small patient requiring low flow and having low blood volume is better served by operating at a low minimum level (low flow allows more time to react before the outlet chamber empties) and a low "high" level setting, the combination minimizing the volume in the air purger. On the other hand, for a large patient that requires high flow and more operating volume, both the low volume and high level sensor would be raised to provide a larger screen area for the higher flow and more volume for the controller to react a low volume condition.

It should be clear that inlet pressure sensed by pressure transducer 32ca shown in FIG. 3aa can send a signal to control unit 33 that controls pump speed in a manner similar to that described level sensor 32. Thus, a low hydraulic pressure sensed at 32ca indicates a low blood level in outlet chamber 3 and signals controller 33 to react to prevent further drop in blood level. During VAVD, a second pressure transducer, 32cb measuring the vacuum applied to the blood chamber, is also used. Here, the signal used for controller 33 is the difference between transducer 32ca and transducer 32cb, the difference being the hydraulic pressure due to the blood level in the chamber.

The air purging chamber allows many new designs not possible with Sate-of-Art devices. For example line drawings of FIGS. 3c and 3d illustrate an air purging reservoir incorporating means to accept vented ("clean") blood. Combining the vented blood directly with the venous blood in chamber 2 is prohibitive because the high volume of air in the vented blood would cause excess foaming. Incorporating an air purging chamber for vented blood at the top of the air purging chamber assures that the large volume of air, so common to vented blood, is eliminated prior to the vented blood combining with the blood in inlet chamber 2. As shown, the top section of the air purging chamber is radially enlarged preferably to 1.5 to 2.5 times the diameter of chamber 3 so channel 20a can accommodate vent chamber 22. Vent chamber 22 is formed of screen wall 22c, much like chamber 2 is formed by screen wall 2c, and incorporates defoamer 15 at the top section of chamber 22. Vent chamber 22 is housed in the enlarged top section of outlet chamber 3 defined by outside cylindrical wall 3cc inside cylindrical screen wall 2cc. Defoamer 20 is contained and may be supported by screen 2cc. Vent chamber is centrally suspended at the top and preferably does not contact venous blood defoamer 20. Annular channel 20a between vent chamber 22 and venous defoamer 20 serves to exhaust venous air. Vented blood enters vent chamber 22 via inlet vent port 23 located atop the air purging chamber and flows downward to bottom 22a of screen 22c. Further, the bottom of screen 22c is sealed on a diagonal with its lowest point contacting fluid path 22b described below. It is important that bottom 23a of vent tube 23 be at a higher level than the maximum blood level 2d of inlet chamber 2. This would assure that the large air volume in the vented blood does not bubble into the venous blood entering chamber 2. Foam associated with the vented blood entering vent chamber 22 is collapsed when contacting defoamer 15 disposed within the inside periphery of vent chamber 22. Preferably, the only fluid communication between port 23 and enlarged channel 20a is via screen 22c. This limits the foam and bubbles from the vented blood from entering channel 20a. Defoamer 20 is supported by circular screen 2cc and defoamer 15 is supported by screen 22c. With the exception noted in the next paragraph, the lower section of air purging chamber 1116a is identical to that described for air purging chamber 1116 in reference to FIG. 3a. Inlet chamber 2 forms unobstructed fluid communication with enlarged channel 20a via thin walled fitting 24. Thus, screen 2c is sealed to the smaller diameter bottom section of fitting 24 and screen 2cc is sealed to the larger diameter top section of fitting 24.

Also shown in FIG. 3c is fluid path 22b between bottom 22a of vent chamber 22 to inlet chamber 2. Path 22b prevents, or at least reduces, splashing where the vented blood enters blood in chamber 2 and combines with venous blood at level 2d. Less splashing results in less air bubbles entrapment and foam formation. Path 22b can be for example polyurethane foam as used for defoamer 20 but without the antifoam agents. Other materials that wick blood and prevent its free fall, such as screens, can also serve as the fluid path. Air entering inlet chamber 2 crosses to outlet chamber 3 along a non wetted screen area and then flows upward to air exhaust tube 3e. Air entrapped within the vented blood entering vent chamber 22, is forced across the non wetted section of screen 22c and then exhausts via port 3e. It should be clear that defoamer 15 may also facilitate defoaming venous blood foam formed in chamber 2.

FIG. 3e illustrates air purger 1116a, shown in FIG. 3c, in its preferred tilted angle of between 10° and 45° and most preferably between 15° and 30°. Angling the air purger allows air bubbles 27 to separate from the blood and move vertically up to higher wall 2c-H and the blood to lower wall 2c-L. Here, fluid path 22b is in contact with screen wall 2c-L. This allows vented blood flowing along path 22b, to continue flowing along screen wall 2c-L thereby further reducing splashing of vented blood as it combines with venous blood in chamber 2 at level 2d.

FIG. 3c also illustrates that a design where bottom 3a of outlet chamber 3 and bottom 2a of inlet chamber 2 can essentially be at the same vertical height. This design reduces the dead space associated with that shown in FIG. 3a where some blood can always be left in inlet tube 1 because its opening is higher than outlet port 4. In this configuration, outlet port 4 has expanded section 4c about the area of screen 2c at bottom 3a of outlet chamber 3 to provide slower and more uniform velocity. Such a design would require that chamber 3 be formed by blow molding or combined by two halves made by vacuum forming or that outlet port be injected molded as a separate piece and fixed to the bottom of chamber 3. Outlet Port 4 can also be aligned parallel to inlet port 1.

Figure 4A:
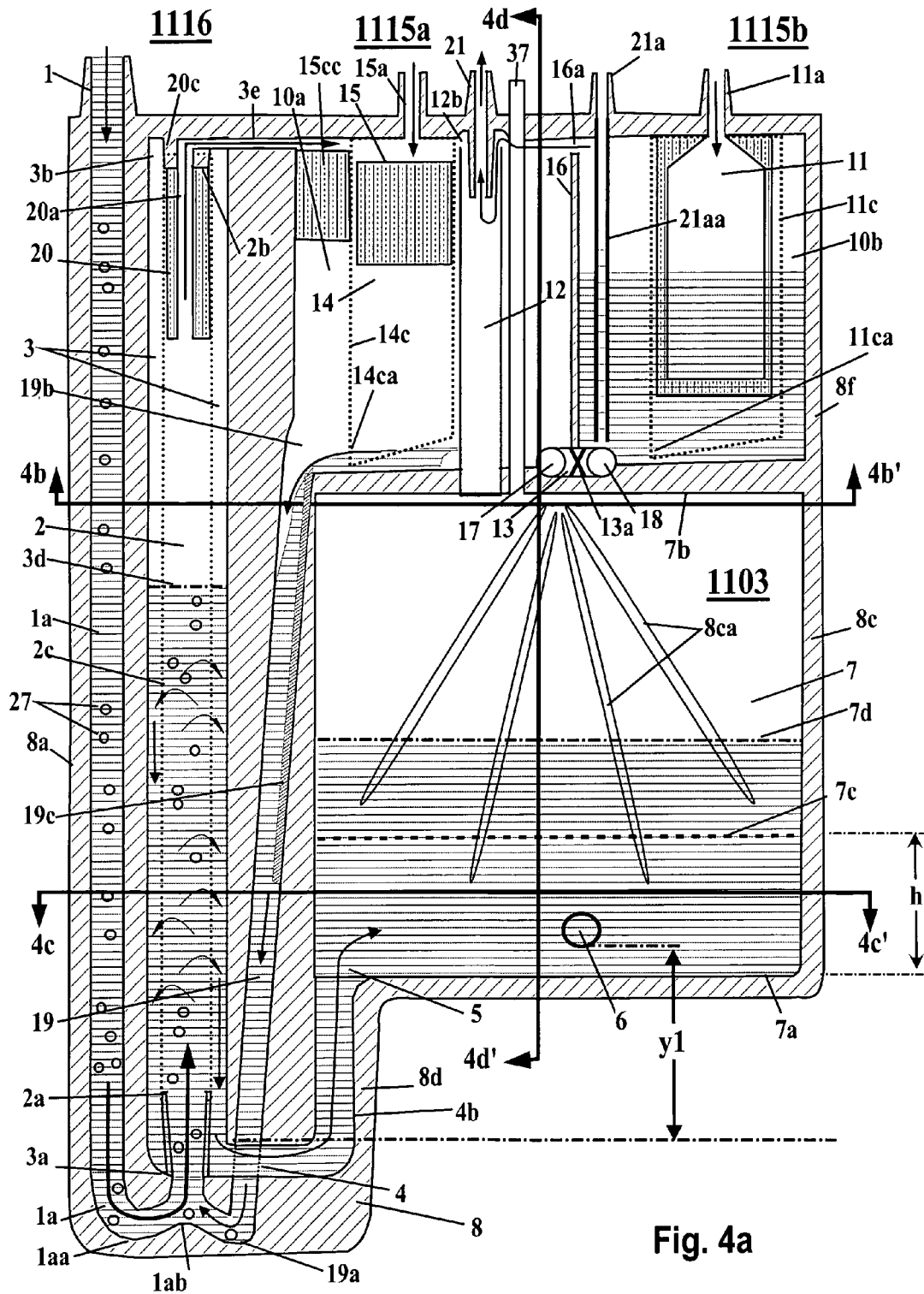
FIG. 4a is a line drawing illustrating one preferred embodiment of the present invention where the air purging chamber shown in FIG. 3a is combined with a venous reservoir having at least one flexible wall and with the innovative two-chambers cardiotomy reservoir.
Figure 4B:
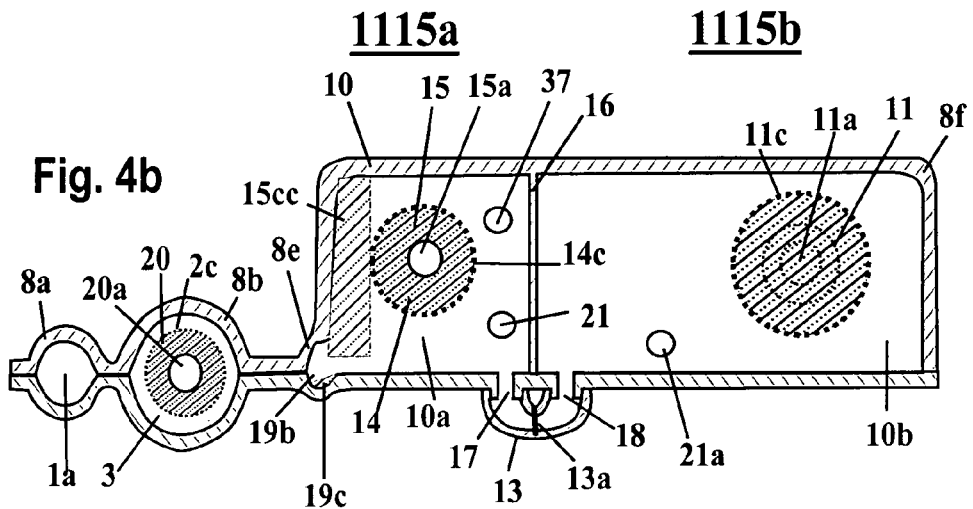
Figure 4C:
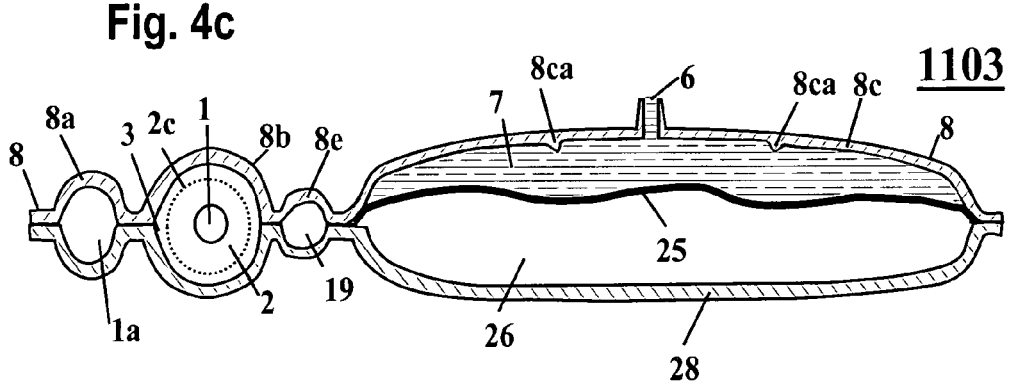
Figure 4D:
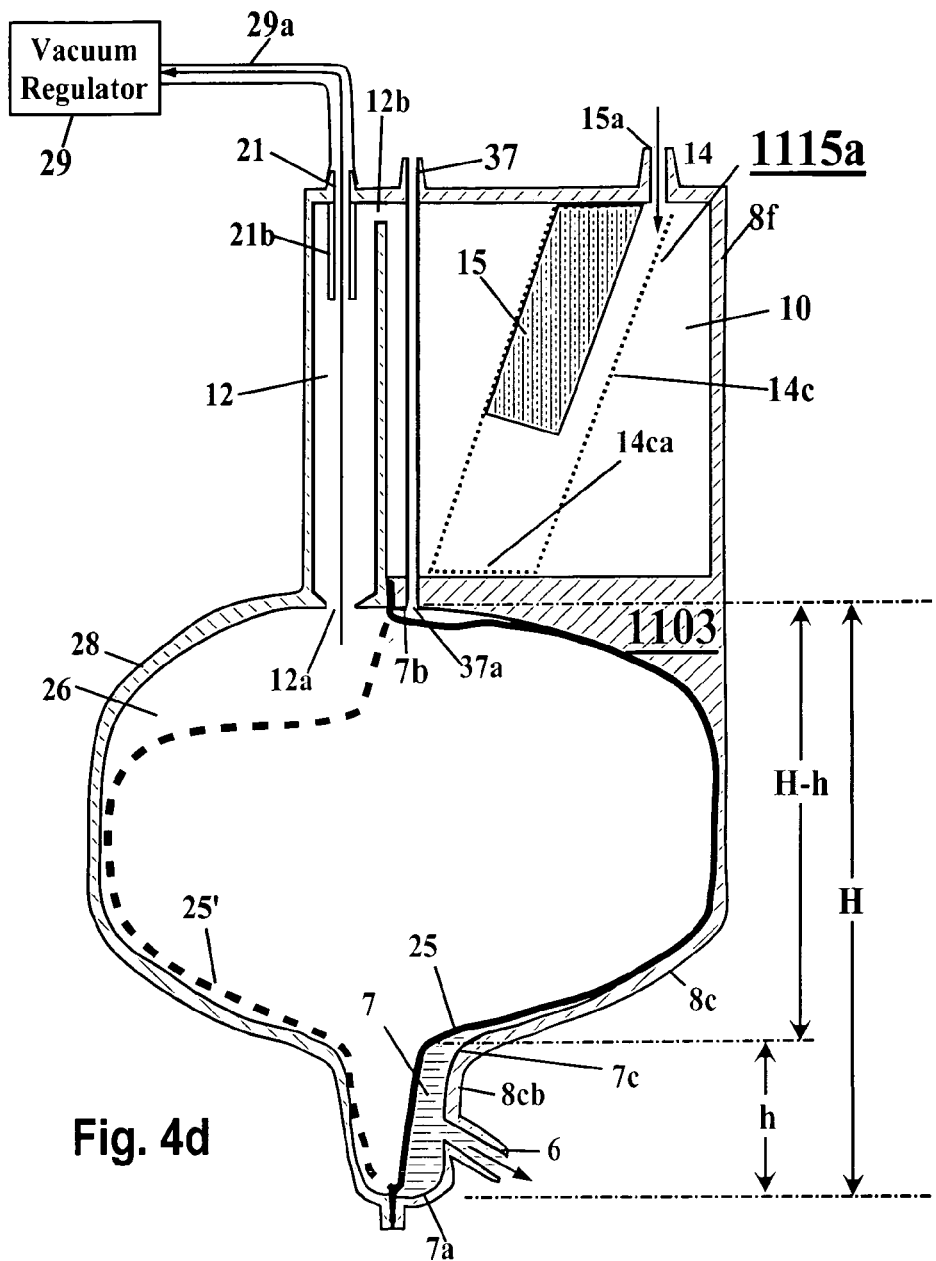

Another preferred means to prevent air from entering blood pump 1104 of FIG. 2 is to combine air purging chamber 1116 with closed compliant chamber 7 having outlet port 6 that shuts off before blood level 3*d* reaches the level of its outlet port 4 of outlet chamber 3. FIG. 4*a* is a line drawing illustrating a front view of a unit combining air purging chamber 1116 with compliant venous reservoir 1103 having at least one pliable wall. As shown, the unit also incorporates dual chamber cardiotomy reservoir (1115*a* and 1115*b* in FIG. 2). A line drawing of a cross sectional view of the combined unit shown in FIG. 4*a* taken along line 4*b*-4*b*' is illustrated in FIG. 4*b*. A line drawing of a cross sectional view of the combined unit shown in FIG. 4*a* taken along line 4*c*-4*c*' is illustrated in FIG. 4*c*. A line drawing of a cross sectional view of the combined unit shown in FIG. 4*a* taken along line 4*d*-4*d*' is illustrated in FIG. 4*d*. Here inlet channel 1*a* extends from top inlet 1 of the combined unit downward to form a fluid communication with inlet chamber 2 of air purging chamber 1116. Air purging chamber 1116 is essentially the same as described in reference to FIGS. 3*a* and 3*b*. Outlet 4 of outlet chamber 3 extends as channel 4*b* to form fluid communication with inlet 5 of compliant storage chamber 7. To assure low resistance to flow in channel 4*b*, preferably channel 4*b* is as short as possible and has an effective diameter of ½ inch. Compliant storage chamber 7 is formed by rigid concaved backwall 8*c* and matching in shape concaved pliable diaphragm 25, seen in FIGS. 4*c* and 4*d*. Diaphragm 25, which can be vacuum-formed from films such as PVC, polyurethane or EVA, nestles in concaved backwall 8*c* and is sealed along its outside periphery to the outside periphery of rigid wall 8*c* to form variable volume closed blood chamber 7. Chamber 7 has an inlet port 5 and outlet port 6, both located along bottom 7*a* of blood chamber 7 as illustrated in FIGS. 4*a* and 4*d*. Blood is pumped from blood chamber 7 via outlet 6 that is in fluid communication with arterial pump 1104, shown in FIG. 2, via typical perfusion tubing (e.g. tube 135 in FIG. 2). As blood fills blood chamber 7, pliable diaphragm 25 moves outward, expanding the volume capacity of chamber 7 to accommodate the additional blood volume. The only air to be removed from chamber 7 is that associated with initial priming of chamber 7. Air in blood chamber 7 is removed through tube 37, shown in FIG. 4*d*, having one open end along top 7*b* of chamber 7 and the other open end accessible for the user to pull the air out. A one-way valve or a stopcock can be adapted to tube 37 to facilitate air removal and preventing its return. Air movement upward in chamber 7 may be enhanced by at least one protrusion 8*ca* incorporated into rigid backwall 8*c*, shown in FIGS. 4*a* and 4*c*. The protrusion serves the same purpose as described in reference to air removal tubes shown in FIG. 1*b* of aforementioned Tamari's U.S. Pat. No. '426. In short, protrusion 8*ca* forms channels between its wall and flexible diaphragm 25 to allow air to move up and be purged via air purging port 37. In addition, protrusions 8*ca* also provide greater strength and stiffness to backwall 8*c*, thereby allowing wall 8*c* to be thinner, reducing its weight and cost. As described below, once primed and air free, no air should enter blood chamber 7, a great advantage over State-of-the-Art venous bags which require constant vigilance, suction to remove that air or some automated means.

The preferred dimensions of compliant chamber 7 depend on its use. For adult patients, the blood volume capacity should be between 1 and 3 liters, but can be reduced to 20 to 500 ml when designed to be used in association with minicircuits. The lowest volume is that required for chamber 7 to provide the shot-off feature of outlet 6 of the compliant chamber 7 described below.

A critical design feature of the combining air purging chamber 1116 with venous reservoir 1103 is that the vertical location of outlet port 4 of the air purging chamber 1116 is below the lowest vertical location of chamber 7 of venous reservoir 1103. Height difference "y1" shown in FIG. 4*a* between top of outlet port 4 and bottom of outlet port 6 should be sufficient to assure that as blood level 3*d* of chamber 3 drops below the bottom of outlet 6 of blood chamber 7, the negative pressure due to the hydraulic height difference between blood level 3*d* and the bottom of outlet 6 is sufficient to cause pliable diaphragm 25, shown in FIGS. 4*c* and 4*d*, to collapse against backwall 8 and close outlet 6. Closed port 6 isolates outlet chamber 3 from the negative pressure generated by pump 1104, shown in FIG. 2 and stops flow out of compliant chamber 7, thereby stops flow out of chamber 3 via outlet port 4 preventing blood level 3*d* from dropping to outlet port 4 and air flowing from emptied blood chamber 3 into blood chamber 7 of venous reservoir 1103. As blood level 3*d* in air purger chamber 3 rises above bottom 7*a* of complaint chamber 7, then blood starts to refill compliant chamber 7 until its outlet 6 reopens.

The aforementioned combination illustrated in FIGS. 4*a-d* and 5*a-b* provides automatic and passive air purging capabilities, as does a hard shell venous reservoir and the clinically preferred close blood chamber as does a soft shell venous reservoir. It also prevents air from entering the compliant venous blood chamber. Any other venous bag that contains air, allows that air to be pumped to the patient when it is drained of blood. With the aforementioned combined unit, air purging is handed in a separate chamber than compliant chamber 7 forming the closed venous reservoir and therefore no air can be pumped to the patient.

The lower section of compliant storage chamber 7, that between bottom 7*a* and transition level 7*c* in FIGS. 4*a* and 4*d* having a height of "h", is shallower, more vertical in shape, and accommodates much less volume per height than the upper section, that between transition 7*c* and upper level 7*b*, defined as "H-h" in FIG. 4*d*. The shallower section provides a larger change in height per unit change in blood volume and therefore a better visualization of small volume changes in that section. The larger increase in blood height also results in a greater force to move compliant diaphragm 25 from a closed position to an open position thereby overcoming the shortfall of prior art venous reservoir as previously described for aforementioned U.S. Pat. No. 4,424,190. The desirable early opening of a closed outlet is further assisted by virtue of outlet port 6 located on lower rigid wall 8*cb* that is flat and close to vertical (e.g. between 70° and 90° of the horizontal plane). The vertical shape allows diaphragm 25 more easily to "peel" away from rigid wall 8*cb* shown in FIG. 4*d*. The depth of the lower section is preferably between ¼" and 1" and most preferably between ⅜" and ⅝". Height "h" of the lower section is preferably between 1" and 4" but can be higher if a low volume compliant storage chamber is desired to better meet minicircuit requirements. To further assure that pliable diaphragm 25 does open without requiring a large volume increase in chamber 7, outlet 6 of chamber 7 is not located at the lowest fluid level of chamber 7, as is the case for prior art compliant venous reservoirs, but preferably at least 1 to 4 lengths of the diameter for outlet port 6 away from bottom 7*a*. This design also enhances intimate contact between diaphragm 25 and rigid backplate 8 and improves the closure of outlet port 6.

It should be clear that when using the air purging chamber for minicircuit applications, compliant chamber 7 can be limited in volume by reducing the chamber to that defined by a height sufficient to allow diaphragm 25 to remain open at the designed blood flows (e.g. 6 liters/min for adult patients) and a blood level in outlet chamber 3 that provides sufficient screen area for efficient air removal. The minimum volume that is needed for minicircuits would have compliant chamber 7 serve as a shut off valve to assure that blood flow from air purging chamber to complaint chamber 7 stops prior to air exiting outlet port 4 of outlet chamber 3. The minimum operating volume of the compliant chamber is preferably between 20 ml and 200 ml. Since blood level 3d can rise above the vertical height of "h" (the maximum height for compliant chamber 7 when used only as a shut off valve) it will provide a higher hydraulic pressure than that afforded by "h". This higher pressure will result in a higher force available to reopen port 6 without the large volume associated with filling section "H-h" shown in FIG. 4d.

It should be noted that if a low level sensor is used with the air purger, then even if outlet 6 of compliant chamber does not fully close, it still would collapse to increase resistance to flow out of complaint chamber 7 and would allow more time for controller 33 to react as previously described. More time allows for greater safety.

The Inventor has shown that bubble counts at the outlet of a venous bag decrease as its blood level increases (Tamari Y, et. al.: A New Top-Loading Venous Bag Provides Vacuum Assisted Venous Drainage. Perfusion 17:383-390, 2002). Thus, the higher blood level in the air purging chamber relative to blood level in the compliant storage chamber is an inherent safety characteristic of the system that assures more favorable conditions for air removal. Further, with State-of-the-Art venous bags, as the blood volume in the bag decreases, the screen area available for blood flow from the inlet to the outlet of the bag decreases. A decrease in the screen area results in an increase in blood velocity across each pore of the screen which can cause more bubbles at the inlet side of the screen to cross to the outlet side of the screen. With the present design, the screened section in the air purging chamber can extend below the bottom of compliant storage chamber 7, assuring that even at very low blood levels in compliant storage chamber 7, the blood column in the air purging chamber is high enough to provide a large screen area to inhibit bubbles in the venous line from reaching the outlet of the compliant storage chamber. This is clearly shown in FIGS. 4a, 5a, 5b and 6 where bottom 2a of screen inlet chamber 2 is vertically lower than bottom 7a of blood chamber 7. Another advantage is that whenever blood flows from the air purging chamber to the compliant storage chamber, the height of the blood column in the air purging chamber is always higher than the blood level in the compliant storage chamber.

FIGS. 5a and 5b are line drawings illustrating the design superiority of the present invention in handling air. In each, air purging chamber 1116 is combined with venous reservoir 1103 in a similar manner to the combined air purging chamber 1116 and venous reservoir 1103 as described in reference to FIGS. 4a, 4c and 4d. Cardiotomy chambers 1115a and 1115b shown in FIGS. 5a and 5b do not affect the discussion below. FIG. 5a illustrates a condition that is most challenging to any venous reservoir: eliminate incoming venous air at low blood volume and high blood flow. With the combined air purging chamber 1116 and venous reservoir 1103, air is handled in an efficient manner by assuring that a large screen area is available. This is achieved by three means. First, bottom 2a of screen 2c forming cylindrical inlet chamber 2 can be located below bottom 7a of blood chamber 7. The height difference between bottom 2a and bottom 7a provides additional screen area with a smaller increase in operating volume than that possible with State-of-the-Art venous bags. Second, the blood volume where air is eliminated (i.e. chamber 2) is present as a tall vertical blood column surrounded by screened wall 2c provides a larger uninhibited screen area than the shallow but wide blood level of the aforementioned state-of-art venous bags that exposes a much smaller effective screen area as described in reference to FIGS. 1a, 1aa, and 1ab. Third, because there is some resistance to flow between outlet chamber 3, outlet port 4, interconnecting channel 4b and inlet port 5 of blood chamber 7, then under any flow conditions, blood level 3d is higher than blood level 7d in blood chamber 7 of venous reservoir 1103 (i.e. the pressure required to overcome the aforementioned resistance to flow).

Further, for any given design, the difference in height between blood level 3d in air purging chamber 1116 and blood level 7d in venous reservoir 1103 increases as blood flow increases as is illustrated by comparing low flow conditions illustrated in FIG. 5b to high flow conditions illustrated in FIG. 5a. This inherent property provides additional safety: at higher flows when a fixed screen area is more vulnerable to bubbles crossing the screen (higher velocity and drag), the current invention presents a larger screen area for blood flow at least partially compensating for the higher flow and keeping the velocity across each pore low.

The inherent difference between blood level 3d in outlet chamber 3 of the air purger and blood level 7d in compliant chamber 7 of the present invention can be manipulated to improve air removal from the incoming venous blood. For example, channel 4b could incorporate an adjustable resistance that controls the height of level 3d relative to level 7d. Thus, at very low volumes, the resistance to flow between chamber 3 and chamber 7 can be increased to maintain higher blood level 3d. Conversely, with a high blood volume in chamber 7 the resistance to flow between chamber 3 and chamber 7 can be decreased because blood level 3d is already high. This can be achieved by incorporating an adjustable resistance, to the flow fluid path between the air purging chamber and compliant storage chamber 7, such as tubing clamp 4bb shown in FIG. 5a, thereby allowing the end user to adjust the height of the blood column in the air purging chamber to accommodate different flow and air volume in the incoming venous blood. It should be noted that simple fluid physics dictates that when blood flow ceases, blood level 3d in chamber 3 equals blood level 7d in venous blood chamber 7. The effective air handling described above, is in direct contrast to prior art soft shell venous reservoirs as previously described in reference illustrated in FIGS. 1a, 1aa and 1ab.

FIGS. 5a and 5b also illustrate that interconnecting channel 4b could form U-shape bottom 4a having a vertical level that is lower than the level of outlet 4. Lower level 4a provides a higher hydraulic pressure to close outlet 6 by pliable film 25 when blood level 3d drops below the level of outlet port 6, as described in reference to FIGS. 4a and 4d. Further, if lowest level 4a is lower than the bottom of outlet 6 of blood chamber 7, then the vertical height of outlet 4 of outlet chamber 3 can be raised above outlet 6.

FIG. 5b illustrates another innovation of the present system; when air purger 1116 is combined with compliant venous reservoir 1103, then interconnecting tube 4b can incorporate one more port in fluid communication via tube 4c with outlet port 6 of reservoir 1103. Tube 4c is also in fluid communication with outlet port 6a. This combination allows the user to clamp outlet port 6 and interconnecting tube 4b (between tube 4c and inlet 5 of reservoir 1103) thereby bypassing reservoir 1103. Bypassing reservoir 1103 allows flowing at a lower operating volume. Thus, one device allows the use of only the venous air purger for cases that do not require much external blood volume capacity (e.g. routine coronary bypass cases) thereby minimizing prime and operating volume. For cases where a large volume capacity is required, tube 4c is clamped between tube 4b and outlet 6a thereby having venous blood flowing through and using the capacity of complaint reservoir 1103.

Yet another advantage of the combined unit described in reference to FIGS. 4a-4d is that it limits the venous blood gas interface to the cross sectional area of outlet chamber 3 and inlet chamber 2 at blood level 3d, an area that is significantly lower than State-of-the-Art hard shell reservoirs. FIG. 8a illustrates that the blood-to-air interface area of the combination of the complaint venous reservoir and venous air purger (APC-VR) is unaffected by the blood volume in the venous bag and is much lower than State-of-the-Art hard shell venous reservoirs. Thus, at a blood level of 1,000 ml, the area of the blood-to-air interface of the air purging chamber having the most preferred dimensions is only between 8 and 15 $cm^2$ compared to 180 $cm^2$ to 305 $cm^2$ for State-of-the-Art hard shell reservoir. At a blood level of 500 ml, the area of the blood to gas interface of the air purging chamber remains between 8 cm and 15 $cm^2$ as compared to an area from 78 $cm^2$ to 305 $cm^2$ for the State-of-the-Art hard shell venous reservoir shown in Table 1. This significant reduction in blood-gas interface results in significant reduction in blood damage and should translate to better clinical outcome. FIG. 8a also shows that the blood-to-air interface area for the stand alone venous air purger (APC-Compound) is also a lower than that of the State-of-the-Art venous reservoirs. The blood-to-air interface area for the former being no more than 50 $cm^2$ at a volume of 500 ml and no more than 80 $cm^2$ at a volume of 800 ml.

FIGS. 4a-4d also illustrate another permutation possible with the present invention: a unitized air purging chamber 1116, compliant blood chamber 7 forming venous reservoir 1103 and a two-chamber ("clean" blood chamber 1115a and "dirty" blood chamber 1115b) cardiotomy reservoir. The two-chamber cardiotomy reservoir shown is for illustrative purposes only. Essentially it is similar to many of the cardiotomy reservoirs in the market (e.g. see cardiotomy reservoir 4 in FIG. 1 of aforementioned U.S. Pat. No. 6,287,270) except that it provides clean blood chamber 10a and dirty blood chamber 10b, separated by wall 16. Cardiotomy section for dirty blood 1115b has at least one inlet port 11a that accepts sucker blood and directs that blood to cardiotomy filter 11 composed of defoamer and a screen and/or felt 11c to filter debris and air associated with suction blood. The filtered blood then accumulates in chamber 10b. Cardiotomy section for clean blood 1115a separates air from the vented blood; it does not need aggressive filter 11 used for dirty blood chamber 10b. Further, the blood filtered in this chamber is "clean", there is no need to store it, and it can be combined with venous blood without concerns for the inflammatory response associated with the dirty blood in chamber 10b. Thus, it needs only screen 14c to reduce the bubble size and volume in the clean blood prior to it combining with the venous blood.

Defoamer 15 used to collapse foam formed by the air in the clean blood in chamber 10a can be much smaller, for example 20% in volume of the defoamer in filter 11 of chamber 10b. Inlet port 15a of clean blood cardiotomy 1115a accepts clean blood and directs it to closed chamber 14 formed, at least partially, by screen wall 14c. Preferably, chamber 14 is angled, as shown in FIG. 4d, a design that has the advantages described by the following example: if the walls of inlet chamber 14 are formed by screen 14c, then air is separated from the blood by having the blood flow across the lower portion of screen 14c while air is removed along the top section of the screen. The pore size of screen 14c is sufficiently small to assure that blood wicks and flows along wall 14c till it reaches bottom 14ca, or blood accumulating in chamber 10, rather than dripping across the screen. This limits splashing and the previously described negative results associated with splashing. Defoamer 15 located along the top section of screened chamber 14 preferably does not contact blood flowing along the lower wall of chamber 14 but is available to collapse blood foam rising to it. The filter for the clean blood is similar to that described in reference to inlet chamber 2 shown in FIGS. 3a and 3b with the exception that the inlet for chamber 14 is at the top. Preferably only blood foam contacts defoamer 15 while vented blood contacts the defoamer only when its level in chamber 10a rises to the level of defoamer 15.

Channel 19 forming the fluid communication between the bottom of the cardiotomy and the inlet to the air purger, is preferably angled to reduce blood velocity as well as allow air bubbles to rise to the top of the moving column as explained in detail in reference to yet to be described channel 153 shown in FIGS. 6 and 6a. The entrance to channel 19, at the bottom of chamber 10a, is widened as indicated by 19b in FIGS. 4a and 4b, a design that allows air bubbles in channel 19 to separate from the flowing blood and escape and thereby limit the air volume trapped as clean blood intermittently flows down channel 19. Channel 19 should have at least the top portion enlarged to an equivalent diameter greater than ⅜" and preferably at least ½". Blood velocity in channel 19 can also be reduced by structure 19c, that can be for example polyurethane foam as used for defoamer 20 but without an antifoam agent. Reducing the blood velocity in channel 19 reduces air bubbles entrapment, especially at the level where the flowing vented blood combines with the blood at the lower level, and foam formation in channel 19. To reduce air from venous blood entering channel 19, lowest level 19a of channel 19 and lowest level 1aa of inlet channel 1a are lower than level 1ab where channel 19 and channel 1a combine and the deaerated vented blood combines with the venous blood.

Chambers 10a and 10b are in fluid communication along their common top wall via always open channel 16a and along their common floor via ports 17 and 18. Ports 17 and 18 are in fluid communication, for example via tubing 13, that can be closed or opened with valve 13a to allow, or prevent, flow of dirty blood into clean chamber 10a and then to combine with the venous blood in chamber 2. As shown in FIG. 4b, valve 13a is a sliding tubing clamp. Dirty blood accumulated in the chamber 10b blood can be removed via port 21a atop chamber 10b, through tubing 21aa with its open end at the bottom of chamber 10b.

Unique clinical advantages are provided by the combination of the two chambers that allow separating clean blood from dirty blood, the ability to store dirty blood or combine it with the venous blood, having an aggressive filter for the dirty blood and an air purger for the clean blood, and reducing the volume of air that is dragged as the vented blood flows down channel 19. It should be clear that the filter for the clean blood consisting of screen 14c and defoamer 15 can also be fitted in channel 20a formed by defoamer 20 located at the top section of inlet chamber 2 in a manner similar to that described in reference to vent chamber 22 shown in FIGS. 3c and 3d.

The volume of chambers 1115a and 1115b can be between 1.0 and 1.5 liters, but preferably, the volume of clean blood chamber 1115a is greater than dirty chamber 1115b. This distribution provides a larger capacity to store venous blood that may overflow from venous reservoir 1103 without that blood contacting filter 11 of dirty chamber 1115b.

It should be understood that at least two of the three units: air purging chamber, compliant chamber and cardiotomy chamber can be combined to form a single unit. For example, it is possible to combine just the cardiotomy and complaint chamber by having those two units share a common rigid wall as described in reference to FIGS. 4a-d but without the air purging chamber as shown by line drawing illustrated in FIG. 7. Since the unit illustrated in FIG. 7 shares the same design for the clean 1115a and dirty 1115b blood chambers combination forming the cardiotomy reservoir, as shown in FIGS. 4a-4d, only the deviations from the unit illustrated in FIGS. 4a-4d are described. The combination unit consists of venous reservoir 7103 having at least one flexible wall and one rigid wall, said walls sealed along their outside periphery to form closed complaint chamber 707 much like compliant chamber 7 previously described in reference to FIGS. 4a-4d. Venous blood enters chamber 707 via inlet port 701 and exits via outlet port 706, both preferably located along bottom 707a of chamber 707. Air entrained in the venous blood is purged via air purging port 703 located along the top most point in chamber 707 and preferably in fluid communication with chambers 710a and 710b of clean and dirty cardiotomies respectfully. Fluid communication of the air side of the cardiotomies and the venous reservoir, allows for air to escape to atmosphere, or for equal vacuum to be applied to all three chambers through single exhaust port 716b. To facilitate use, channel 703 preferably extends up to the top of the cardiotomy reservoir. Channel 703 preferably is large in diameter (e.g. ½" ID) to form a low resistance channel for air bubbles to move up the blood column in channel 703. Defoamer 720 may be located along the top 707b of compliant chamber 707 and may also extend into air purging port 703 (shown as 720a). Air sensor 732 may also be added for the same purpose and function as previously described in reference to sensor 32 in FIGS. 3a and 3aa. The addition of a defoamer to the top of compliant chamber 707 and or air purging port 703 is to aggressively collapse foam thereby reduce the large blood-air interface associated with foam. This method also allows port 703 to attach to a regulated vacuum source (not shown) to purge the air without the need to pump the foam out of chamber 707 and without the need to have the foam/blood exiting port 703 to contact the aggressive filter of a cardiotomy reservoir.

FIG. 7 shows that outlet port 706 is located in the lower portion of chamber 707 and is designed with considerations previously described for outlet 6 shown in reference to FIGS. 4a-4d. Thus, level 719a is vertically lower than outlet port 706. This assures that outlet port 706 closes prior to blood level 719d in channel 719 drops to lowest point 719a of channel 719. As described before in reference to port 6 closing, when the blood in chamber 707 empties, the negative pressure due to the hydraulic height difference between 719a of channel 719 and outlet 706 of blood chamber 707 is sufficient for the flexible wall of chamber 707 to collapse against the opening of outlet 706, closing that port, preventing further emptying of blood chamber 707 and preventing air from passing point 719a and into chamber 707.

The unit shown in FIG. 7 does not have an air purger such as 1116 shown in FIG. 6. It therefore does incorporate a screen (not shown) between inlet port 705 and outlet port 706.

The dual chamber cardiotomy reservoir atop the venous reservoir is almost identical to that described in reference to clean 1115a and dirty 1115b blood chambers shown in FIGS. 4a-4d. It has one large chamber 710 divided by separating wall 716 into chamber 710a for clean blood and chamber 710b for dirty blood. Wall 716 extends from the bottom to the top of chamber 710 leaving a fluid communication 716a between the top of chambers 710a and 710b. Since clean blood need not be kept out of closed compliant chamber 707, then the volume of chamber 710a need only be sufficient to accommodate the screened chamber 714 used to deaerate and defoam the clean blood. Thus, most of the volume in the cardiotomy can be assigned to chamber 710b, thereby maximizing the volume available for dirty blood at the expense of volume for the clean blood. If there is no need for additional blood holding capacity than that available in compliant chamber 707 then the volume of chamber 710a should be no more than 20%, of the volume of chamber 710b. Clean blood enters via port 715a into clean chamber 714 formed of screen wall 714c that is sealed at its bottom. Defoamer 715 positioned at the top section of chamber 714 collapses foam in chamber 714. Clean blood flows through screen 714c, with the screen reducing the bubble size and air volume in the exiting clean blood. Similarly, dirty blood enters via port 711a into aggressive filter 711 that also includes a defoaming agent. The filtered dirty blood flows into chamber 710b where it can be stored or flow to chamber 710a via port 718 and 717. Ports 717 and 718 are in fluid communication via tubing 713 that can be closed or opened with valve 713a to allow or prevent the dirty blood to flow to clean chamber 710a and then to combine with the venous blood in chamber 707. Blood in chamber 710a flows down channel 719 and combines with venous blood at inlet port 701. It is preferred that lowest vertical level 719a of channel 719 is lower than inlet port 701 and that inlet port 701 is bottom 707a of chamber 707. This minimizes air from the venous blood rising into channel 719 or air from channel 719 rising up venous line via inlet port 701.

It should be obvious that it may be advantageous to have clean blood chamber 1115a larger than dirty blood 1115b, for example for patients with a large blood volume that needs to be stored without it contacting the filter of the dirty blood.

FIGS. 4c and 4d also illustrate that compliant blood chamber 7 can be fitted with front plate 28 sealed along the outside periphery of wall 8c to form sealed air chamber 26 with flexible diaphragm 25 as one wall and front plate 28 as the other wall. Channel 12 forms a fluid communication between air chamber 26 at opening 12a and cardiotomy reservoir chamber 10 at opening 12b assuring that the air pressure in these two chambers is equal. Exhaust port 21 in fluid communication with chamber 10 is open to ambient atmosphere, or as shown in FIG. 4d, in fluid communication with vacuum regulator 29. The latter can be used for vacuum assisted venous return (VAVD). Note that exhaust port 21 is in fluid communication with the air side of chamber 10a of the clean blood, chamber 10b of the dirty blood, and inlet chamber 2 and outlet chamber 3 of the air purging chamber. It is also in fluid communication with the air side of diaphragm 25. This allows a single port to apply vacuum to all four chambers. Freely moving compliant diaphragm 25 assures that the blood pressure in compliant storage chamber 7 equals the air pressure in air chamber 26. Thus, when vacuum is applied to port 21, it is transmitted to air chamber 10, and then via channel 12, to air chamber 26 and then, to the air side of moving diaphragm 25, to the blood side of diaphragm 25 forming the flexible wall of chamber 7. This design is much like that described in reference to FIGS. 10a, 10b and 10c of aforementioned Tamari's '049 patent, vacuum can be applied to flexible diaphragm 25 that allows vacuum assisted venous drainage (VAVD). The shape of front plate 28 preferably is similar in shape to the shape of diaphragm 25 thereby allowing diaphragm 25 to fully expand and maximize the volume chamber 7 can fill to with blood. The same vacuum is also applied to inlet chamber 2 and outlet chamber 3 of air purging chamber 1116 via channel 3e shown in FIGS. 4a and 5a and 5b. Thus, the unrestricted fluid communication between air chamber 26 and cardiotomy chamber 10 and between cardiotomy chamber and inlet chamber 2 and outlet chamber 3 of air purging chamber 1116 (or 1116a) allows a single air port in any of these chambers to be used to apply vacuum to the other chambers and maintain these other chambers at the same vacuum as the chamber with that single air port. In the example shown that port is port 21 atop chamber 10 of cardiotomy 111a shown in FIGS. 4a, 4b and 4d.

As previously described, during VAVD it is necessary to trap water vapor in the air exhausted from the venous/cardiotomy reservoir that condenses on the cooler walls of the vacuum tubing and prevent the condensate from dripping back into the blood. FIGS. 4a and 4d show another innovation: a vapor trap incorporated into the reservoir designed for VAVD. For example, bottom section 21b of exhaust port 21, extends below the top of chamber 12. The top of chamber 12 is in fluid communication with the air space above clean chamber 1115a and dirty chamber 1115b and the bottom of chamber 12 is in fluid communication with air chamber 26 of venous reservoir 1103. Thus, any water condensate that drips down out of exhaust tube 21b, falls into, and is trapped by, chamber 12 and eventually flows into air chamber 26 of venous reservoir 1103.

It should be understood that the description for gravity drainage (i.e. no vacuum applied to any port), where air is purged to atmosphere, also applies to VAVD applications except "atmosphere" is changed to the vacuum applied.

As shown in FIGS. 4a to 4d, air purging chamber 1116, venous reservoir 1103, cardiotomy reservoir 1115, as well as channels 1, 3e, 4 and 12 interconnecting these chambers, are at least partially formed with common rigid plate 8, a design that reduces manufacturing costs and simplifies setup. Thus for example, rigid wall 8a forms at least a part of the wall forming inlet channel 1a of air purging chamber 1116; rigid wall 8b forms at least one part of the wall forming outlet chamber 3 of air purging chamber 1116; rigid wall 8c forms at least a part of the wall forming compliant storage chamber 7; rigid wall 8d forms at least a part of channel 4b connecting outlet chamber 3 to compliant storage chamber 7; rigid wall 8e forms channel 19 connecting chamber 10 of cardiotomy 1115 to the bottom of inlet channel 1; rigid wall 8f forms at least one part of the wall forming chamber 10 of cardiotomy 1115. Common wall 8 may also form channel 3e connecting the top of outlet chamber 3 to the top chamber 10 of cardiotomy 1115, outlet port 6 of compliant storage chamber 7 as well as the numerous connectors atop cardiotomy reservoir 1115.

It should be clear that rigid wall 8 can have a matching clamshell like mirror image structure that fits to complete the walls required to form the aforementioned chambers and channels. Other designs include having outlet chamber 3 and cardiotomy chamber 10 with its divider 16, and concave section 8c injected molded and then fitted with top covers that incorporate ports such as air port 21 or inlet port 1a shown in FIG. 4a.

FIG. 6 is a line drawing illustrating a design where tubing is used as channel 4b connecting outlet 4 of the air purging chamber, previously described in reference to FIGS. 3a-3d, to compliant reservoir 7, and tubing 153 is used to connect the outlet of cardiotomy reservoir to inlet 1 of air purging chamber 1116. Using tubing has two advantages: it simplifies the mold and it enables the user to clamp off the tubing when needed. It also illustrates that air purging chamber 1116 can be used with State-of-the-Art venous bags eliminating air from entering the bag to provide greater safety.

FIG. 6 also illustrates another means to reduce air being dragged from cardiotomy 1115 to inlet chamber 2 via channel 153. Here tube 153 is slanted to allow air bubbles 27 that have entered tube 153 to rise to the radial top of channel 153 and then, as illustrated in FIG. 6a by the upward pointing arrow, move up channel 153 along its top most wall. Raised section 159a of outlet port 159 located at the bottom of cardiotomy 1115, facilitates air bubble escape from channel 153 by preventing blood from entering channel 153 at highest outlet point 159a where air escapes from tube 153 during intermittent blood flow. To further reduce air bubbles entrapment and facilitate air bubbles movement up channel 153, channel 153 should have at least its top portion enlarged to an equivalent diameter greater than 3/8" and preferably at least 1/2" and incorporate structure 153c serving the same function as structure 19c previously described in reference to FIG. 4a.

Incorporating all the elements of the invention provides a closed venous reservoir that:
1) Has superb air handling.
2) Passively removes air.
3) Primes easier and faster than any other closed venous reservoir.
4) Incorporates a cardiotomy reservoir and allows VAVD.
5) Deaerates vented (clean) blood without that blood contacting the filter of dirty blood cardiotomy by incorporating an innovative two chamber cardiotomy reservoir.
6) Shuts off when empty and requires little volume to reopen.
7) It can operate at low volume without the danger of pumping air.
8) Once primed, air cannot enter it. The new reservoir is therefore safer.
9) A low level alarm can be placed on it as easily as on any hard shell venous reservoir.
10) Has the lowest blood-to-air interface of any hardshell reservoirs.
11) Has the highest ratio of screen area to blood-to-air interface.
12) Its air purging chamber can be used with or without its compliant chamber allowing lower operating volume.

It should be understood that a comprehensive description of each of the applications of the invention is beyond the scope of a patent application and therefore the aforementioned descriptions are given as illustrations and should not be used to limit the intent, spirit, or scope of the invention.

With that in mind, I claim:

1. A passive air purging system to trap and remove air bubbles from venous blood of a patient, undergoing cardiopulmonary bypass using a pump to generate blood pressure, said pump having a pump inlet, the air purging system comprising:
   a) an air purging blood chamber defined by one or more vertical walls and a first bottom, and a top at a first height, the air purging blood chamber adapted to contain blood and air wherein an interface between the blood and the air occurs at a second height from the first bottom, the chamber having a first horizontal cross section at the second height, said air purging blood chamber having:
      (i) a first inlet port;
      (ii) a first outlet port;
      (iii) an air exhaust port in fluid communication with ambient atmosphere;
   b) a screen interposed between the first inlet port and the first outlet port, the screen dividing the air purging blood chamber to define a first outlet chamber and a first inlet chamber with the first inlet port entering the first inlet chamber and the first outlet port exiting the first outlet chamber, the screen providing fluid communication between the first inlet port and the first outlet port and inhibiting air bubbles entering the first inlet port from reaching the first outlet port; and c) a structure to handle a venous blood flow of at least 3.5 liters/min;

wherein, the air purging system is structured to allow air in the venous blood that enters the first inlet chamber, to rise to the second height in the first inlet chamber where the air is passively purged to the ambient atmosphere and wherein the first horizontal cross section at the second height is less than 60 $cm^2$ for at least 14 cm from the first bottom.

2. An air purging system as claimed in claim 1, further comprising means to maintain the second height above the first outlet port thereby preventing gross air from exiting the first outlet port.

3. An air purging system of claim 2, further comprising a second blood level maintaining means for maintaining the second height below the air exhaust port thereby preventing blood from reaching and spilling out of the air exhaust port.

4. An air purging system as claimed in claim 1, further comprising a second blood level maintaining means to assure that the second height does not reach and venous blood does not spill out of the air exhaust port.

5. An air purging system as claimed in claim 4, wherein the second blood level maintaining means comprises a sensor operably connected to a controller, the sensor being capable of detecting the second height and sending a signal to the controller, the controller being capable of at least one of alarming the user, increasing outlet flow, and decreasing inflow such that the second height does not reach and the blood does not spill out of the air exhaust port.

6. An air purging system as claimed in claim 4 wherein the second blood level maintaining means comprises an air exhaust tube extending from the air exhaust port towards a level of the patient such that blood flow from the patient into the air purging blood chamber decreases as the blood level in the air exhaust tube rises.

7. An air purging system as claimed in claim 6 wherein the air exhaust tube is extended to a third height such that blood flow from the patient into the air purging chamber stops once the blood level in the air exhaust tube reaches the level of the patient.

8. An air purging system as claimed in claim 6 wherein the air exhaust tube has an internal diameter of at least ⅜".

9. An air purging system as claimed in claim 6, wherein both the air exhaust tube and the exhaust port have an internal diameter that is at least ½".

10. An air purging system as claimed in claim 1, wherein the screen has a pore size between 20μ and 150μ.

11. An air purging system as claimed in claim 1, wherein the first horizontal cross section is larger than 10 $cm^2$ and smaller than 60 $cm^2$ for at least 18 cm from the first bottom.

12. An air purging system as claimed in claim 1, further comprising a venous line having a cross sectional area between the patient and the first inlet port of the air purging blood chamber, wherein the screen has an annular cross sectional area, defined by a first cross sectional area of the outlet chamber less a second cross sectional area of the first inlet chamber, that equals at least the cross sectional area of the venous line.

13. An air purging system as claimed in claim 1, further comprising defoaming means for defoaming the blood.

14. An air purging system as claimed in claim 13, wherein the defoaming means comprises a defoamer located in a defoaming chamber positioned above the top section of the first inlet chamber.

15. An air purging system as claimed in claim 14, further comprising a second air purging chamber for air purging and defoaming clean blood, the second air purging blood chamber having a cross sectional area, an inlet for the clean blood and an outlet in fluid communication with the air purging blood chamber.

16. An air purging system as claimed in claim 15, wherein the second air purging chamber is located within the top of the air purging blood chamber for venous blood.

17. An air purging system as claimed in claim 16, wherein the cross sectional area of the second air purging chamber is larger than the cross sectional area of the air purging blood chamber for the venous blood not housing the defoamer for deaerating and defoaming the clean blood.

18. An air purging system as claimed in claim 16 wherein the air purging blood chamber and the second chamber share at least one defoamer.

19. An air purging system as claimed in claim 15 wherein the purged air in the clean blood is exhausted via the air exhaust port.

20. An air purging system as claimed in claim 19, wherein the air purging blood chamber and the second chamber are configured wherein vacuum applied to the air exhaust, applies equal vacuum to the blood in the second chamber and the venous blood in the air purging blood chamber thereby allowing vacuum assisted venous drainage.

21. An air purging system as claimed in claim 14, wherein the defoaming chamber above the top section of the first inlet chamber housing the defoamer for the venous blood has a larger horizontal cross sectional area then that of the air purging blood chamber.

22. An air purging system as claimed in claim 13, wherein the defoaming means comprises a first defoaming section disposed within the first inlet chamber, and a second defoaming section that is smaller than the first defoaming section and extends below the first defoaming section.

23. An air purging system as claimed in claim 22, wherein the second defoaming section comprises an extension that extends downward into the first inlet chamber.

24. An air purging system as claimed in claim 23, wherein the extension has a length that equals up to 75% of the distance between the first bottom and the first height of the air purging blood chamber.

25. An air purging system as claimed in claim 22, wherein further the first inlet chamber has a first inside periphery and wherein the width of the second defoaming section equals from 10% to 50% of the first inside periphery of the first inlet chamber.

26. An air purging system as claimed in claim 1, further comprising a second chamber for air purging, defoaming, and filtering dirty blood, the second chamber having an inlet for incoming dirty blood and an outlet in fluid communication with the air purging blood chamber for the venous blood.

27. An air purging system as claimed in claim 26, further comprising means to reduce splashing of filtered dirty blood as that blood enters the air purging blood chamber and merges with the venous blood.

28. An air purging system as claimed in claim 27, wherein the means to reduce splashing of filtered dirty blood having at least a portion of the fluid communication between the outlet of the second chamber and the first air purging blood chamber at an angle between 10° and 45° off the vertical, said angle allowing the filtered blood to flow downward and air to escape upward.

29. An air purging system as claimed in claim 26, wherein the outlet of the second chamber is in fluid communication with the inlet of the first inlet chamber of the air purging blood chamber thereby having the filtered dirty blood filtered again by the screen between the first inlet port and first outlet port of the air purging blood chamber.

30. An air purging system as claimed in claim 26, further comprising a means to allow the end user to close and open the fluid communication between the outlet of the second chamber and the air purging blood chamber.

31. An air purging system as claimed in claim 26, wherein the air in the blood entering the air purging blood chamber and the second chamber is purged a single air exhaust port.

32. An air purging system as claimed in claim 31, wherein the air purging blood chamber and the second chamber are configured wherein vacuum applied to the single air exhaust port, applies equal vacuum to the blood in the second chamber and the venous blood in the air purging blood chamber thereby allowing vacuum assisted venous drainage.

33. An air purging system as claimed in claim 32, further comprising a vapor trap located below the air exhaust port, thereby eliminating the need for a standalone vapor trap used with prior art reservoirs.

34. An air purging system as claimed in claim 1, wherein the second height is at least 16 cm.

35. An air purging system as claimed in claim 1, wherein the first horizontal cross section is less than 45 cm$^2$.

36. An air purging system as claimed in claim 1, wherein the first horizontal cross section is less than 35 cm$^2$.

37. An air purging system as claimed in claim 1, wherein the first horizontal cross section is less than 25 cm$^2$ at a second height of at least 12 cm.

38. An air purging system as claimed in claim 1, wherein for an air purging system designed for infants having a maximum blood flow that is less than 1.6 liters/min, the first horizontal cross section is less than 20 cm$^2$ at a second height of at least 10 cm.

39. An air purging system as claimed in claim 38, wherein the first horizontal cross section is less than 6 cm2 at a second height of at least 8 cm and wherein the maximum blood flow is less than 1.0 liters/min.

40. An air purging system as claimed in claim 1, further incorporating a venous reservoir to store venous blood, said venous reservoir comprising:
  vi. at least one rigid wall;
  vii. an inlet in fluid communication with the first outlet port of the air purging blood chamber;
  viii. an outlet in fluid communication with the inlet of the pump;
  ix. means to remove air trapped in the venous reservoir; and
  x. a pliable diaphragm forming another wall, said diaphragm having a blood side and an air side;
wherein the air purging system is structured to remove air from the venous blood to maintain the venous reservoir air free.

41. An air purging system as claimed in claim 40, wherein the air purging blood chamber and the venous reservoir are configured such that applying vacuum to the air exhaust port, applies equal vacuum to the air side of the diaphragm of the venous reservoir and the blood in the air purging blood chamber thereby allowing vacuum assisted venous drainage.

42. An air purging system as claimed in claim 41, further comprising a vapor trap located below the air exhaust port, thereby eliminating the need for a standalone vapor trap used with prior art reservoirs.

43. An air purging system as claimed in claim 40, wherein the venous reservoir is structured such that its outlet shuts off prior to air entering its inlet.

44. An air purging system as claimed in claim 43, wherein the outlet of the venous reservoir shuts off prior to air entering the venous reservoir by the pliable diaphragm moving against, and shutting off, the outlet of the venous reservoir, thereby stopping the flow through the outlet of the venous reservoir.

45. An air purging system as claimed in claim 44, wherein shutting off the flow through the outlet of the venous reservoir is achieved by having the lowest point along the fluid communication between the outlet of the air purging blood chamber and the inlet of the venous reservoir, vertically lower than the outlet of the venous reservoir thereby, when a blood level between the outlet port of the air purging blood chamber and the inlet to the venous reservoir falls below the outlet of the venous reservoir, a negative pressure is created at outlet of the venous reservoir that causes the pliable diaphragm of the venous reservoir to seal against the outlet of the venous reservoir.

46. An air purging system as claimed in claim 40, wherein the screen area available for blood flow, said area defined by area of screen wetted by the venous blood, between the inlet port and outlet port of the air purging blood chamber is at least equal to first horizontal cross section and continuously increases relative to the first horizontal cross section as the blood volume in the venous reservoir increases.

47. An air purging system as claimed in claim 1, wherein further, the air purging blood chamber is configured to have a ratio of screen area available for blood flow, said area defined by area of screen wetted by blood, between the inlet port and outlet port and the first horizontal cross section, wherein further, at a blood volume of 300 ml, the ratio is at least 4.5 and the ratio increasing as the second height increases.

48. An air purging system as claimed in claim 47, wherein at a blood volume of 200 ml, the ratio is at least 5.0 and it is increasing as the blood volume in the air purging blood chamber increases.

49. An air purging system as claimed in claim 1, wherein the first inlet port is positioned along the top of the air purging blood chamber with a tubing connected to its bottom and extending downward into the inlet chamber.

50. A passive air purging system to trap and remove air bubbles from venous blood of a patient, undergoing cardiopulmonary bypass using a pump that generates blood pressure, the air purging system comprising:
  (i) a blood chamber with at least one wall being a pliable diaphragm, said diaphragm having a blood side and an air side and structured to stop flow through the outlet when the blood chamber empties;
  (ii) at least one inlet to the blood chamber;
  (iii) at least one outlet from the blood chamber;
  (iv) a blood capacity greater than 600 ml;
  (v) a low blood-air interface that is less than 50 cm$^2$ at a blood volume of greater than 600 ml;
  (vi) means for passively purging air in the venous blood via an air exhaust port; and
  (vii) a screen in the blood path between an inlet to and an outlet from the blood chamber;
wherein the blood capacity allows safe operation at blood flows of at least 4 liters/min, the low blood-air interface reduces blood damage, and the diaphragm stopping flow through at least one outlet prevents air from reaching the pump.

51. An air purging system as claimed in claim 50, wherein the blood capacity is at least 1,000 ml.

52. An air purging system as claimed in claim 50, wherein the passive air purging system is structured to operate safely at a blood flow of less than 2 liters/min, and the blood-air interface is less than 40 cm$^2$ and greater than 4 cm$^2$.

53. An air purging system as claimed in claim 50, wherein the blood capacity is at least 500 ml, the blood-air interface is less than 20 cm$^2$ and greater than 4 cm$^2$.

54. An air purging system as claimed in claim 50, wherein the passive air purging system is structured to operate safely at a blood flow of at least 1.0 liters/min, and the blood-air interface is less than 20 cm$^2$ and greater than 4 cm$^2$.

55. An air purging system as claimed in claim 50, wherein the passive air purging system is structured to operate safely at a maximum blood flow of less than 1.0 liters/min, and the blood-air interface is less than 10 cm$^2$.

56. An air purging system as claimed in claim 50, wherein the first inlet port is positioned along the top of the air purging blood chamber with a tubing connected to its bottom and extending downward into the inlet chamber.

57. A passive venous air purging system and blood handling capacity that traps and removes air bubbles from venous blood of a patient, undergoing cardiopulmonary bypass, the system comprising:
   a) an air purging blood chamber defined by one or more vertical walls and a first bottom, and a top at a first height, the air purging blood chamber adapted to contain blood and air wherein an interface between the blood and the air occurs at a second height from the first bottom, the chamber having a first horizontal cross section at the second height, said blood chamber having:
      (i) a first inlet port;
      (ii) a first outlet port;
      (iii) an air exhaust port in fluid communication with ambient atmosphere;
      (iv) a screen interposed between the first inlet port and the first outlet port, the screen dividing the air purging blood chamber to define a first outlet chamber and a first inlet chamber with the first inlet port entering the first inlet chamber and the first outlet port exiting the first outlet chamber, the screen providing fluid communication between the first inlet port and the first outlet port and inhibiting air bubbles entering the first inlet port from reaching the first outlet port;
      (v) a defoamer to defoam venous blood;
   b) a venous reservoir for storing venous blood, said venous reservoir having at least one rigid wall and one wall being a pliable diaphragm, said diaphragm having a blood side and an air side, said walls forming a chamber to contain venous blood air free, an inlet in fluid communication with the first outlet port of the air purging blood chamber, an outlet, means to remove air trapped in the venous reservoir;
wherein the air purging system is structured to allow air that enters the venous blood in the first inlet chamber to rise to the second height in the first inlet chamber where the air is passively purged to the ambient atmosphere and the combination of the venous reservoir and the air purging blood chamber are structured to remove air from the venous blood to maintain the venous reservoir air free and wherein further wherein the first horizontal cross section is less than 60 cm$^2$ for a second height that extends at least 12 cm;
and wherein further at least one more chamber comprising:
   c) a second chamber for air purging and a defoamer to defoaming clean blood, the second chamber having an inlet for the clean blood and an outlet in fluid communication with the air purging blood chamber and a defoamer to defoam clean blood;
   d) a third chamber for air purging, defoaming, and filtering dirty blood, the third chamber having an inlet for incoming dirty blood and an outlet in fluid communication with the first air purging blood chamber and a defoamer to defoam the dirty blood.

58. An air purging system as claimed in claim 57, wherein the screen interposed between the first inlet port and the first outlet port of the air purging chamber has a bottom and a top, with the bottom of the screen located above the first outlet of the first outlet port.

59. An air purging system as claimed in claim 57 wherein passive venous air purging system comprises the second and third air purging chambers and wherein further the system accommodates at least 1,500 ml of venous blood without the venous blood contacting any of the defoamers.

60. An air purging system as claimed in claim 1, wherein the screen is further configured to have an area available for blood flow between the inlet port and outlet port of the air purging blood chamber, said area defined by area of screen wetted by the venous blood, said area being at least four times larger than the first horizontal cross section when the blood volume is more than 200 ml.

61. A passive air purging system to trap and remove air bubbles from venous blood of a patient, undergoing cardiopulmonary bypass using a pump to generate blood pressure, said pump having a pump inlet, the air purging system comprising:
   a) an air purging blood chamber defined by one or more vertical walls and a first bottom, and a top at a first height, the air purging blood chamber adapted to contain blood and air wherein an interface between the blood and the air occurs at a second height from the first bottom, the chamber having a first horizontal cross section at the second height, said air purging blood chamber having:
      (i) a first inlet port;
      (ii) a first outlet port;
      (iii) an air exhaust port in fluid communication with ambient atmosphere;
      (iv) a defoamer to collapse blood foam;
      (v) a perimeter of the first horizontal cross sectional area;
      (vi) a hydraulic diameter defined as four times the first horizontal cross sectional area divided by the perimeter,
   b) a screen interposed between the first inlet port and the first outlet port, the screen dividing the air purging blood chamber to define a first outlet chamber and a first inlet chamber with the first inlet port entering the first inlet chamber and the first outlet port exiting the first outlet chamber, the screen providing fluid communication between the first inlet port and the first outlet port and inhibiting air bubbles entering the first inlet port from reaching the first outlet port; and
wherein, the air purging system is structured to allow air in the venous blood that enters the first inlet chamber, to rise to the second height in the first inlet chamber where the air is passively purged to the ambient atmosphere and wherein further the second height is at least two times larger than the hydraulic diameter along at least at one point between the first bottom and first height.

* * * * *